Figure 1A:
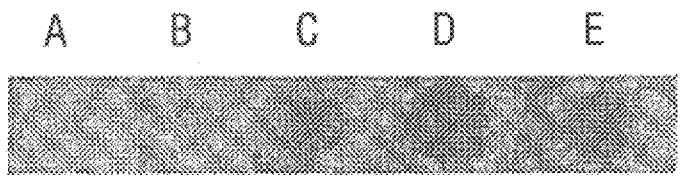

US006083715A

United States Patent [19]
Georgiou et al.

[11] Patent Number: 6,083,715
[45] Date of Patent: Jul. 4, 2000

[54] METHODS FOR PRODUCING HETEROLOGOUS DISULFIDE BOND-CONTAINING POLYPEPTIDES IN BACTERIAL CELLS

[75] Inventors: George Georgiou; Ji Oiu; Paul Bessette, all of Austin, Tex.; James Swartz, Menlo Park, Calif.

[73] Assignees: Board of Regents, The University of Texas System, Austin, Tex.; Genentech, Inc., South San Francisco, Calif.

[21] Appl. No.: 08/871,483

[22] Filed: Jun. 9, 1997

[51] Int. Cl.[7] .............................. C12P 21/06; C12N 1/12; C12N 5/00; C07H 21/02

[52] U.S. Cl. ................... 435/69.1; 435/69.7; 435/252.1; 435/252.8; 435/320.1; 536/23.1; 536/23.4

[58] Field of Search ................................ 435/69.1, 69.7, 435/252.1, 252.8, 320.1; 536/23.1, 23.4

[56] References Cited

U.S. PATENT DOCUMENTS

| | | | |
|---|---|---|---|
| 4,431,740 | 2/1984 | Bell et al. | 435/252.33 |
| 4,652,525 | 3/1987 | Rutter et al. | 435/252.33 |
| 4,661,453 | 4/1987 | Pollard | 435/212 |
| 5,077,392 | 12/1991 | Rudolph et al. | 530/387.1 |
| 5,122,457 | 6/1992 | Reim et al. | 435/69.1 |
| 5,139,939 | 8/1992 | Ohashi et al. | 435/70.1 |
| 5,223,256 | 6/1993 | Stern et al. | 424/94.63 |
| 5,223,408 | 6/1993 | Goeddel et al. | 435/69.3 |
| 5,270,181 | 12/1993 | McCoy et al. | 435/69.7 |
| 5,292,646 | 3/1994 | McCoy et al. | 435/69.7 |
| 5,304,472 | 4/1994 | Bass et al. | 435/69.1 |
| 5,336,602 | 8/1994 | Brinkmann et al. | 435/69.1 |
| 5,342,763 | 8/1994 | Swartz | 435/69.1 |
| 5,453,363 | 9/1995 | Rudolph et al. | 435/69.1 |
| 5,453,364 | 9/1995 | Paoletti | 435/69.3 |
| 5,486,471 | 1/1996 | Mulvihill et al. | 435/226 |
| 5,508,192 | 4/1996 | Georgiou et al. | 435/252.8 |
| 5,578,466 | 11/1996 | Hayano et al. | 435/69.7 |
| 5,616,486 | 4/1997 | Anderson et al. | 435/226 |
| 5,639,635 | 6/1997 | Joly et al. | 435/69.1 |

FOREIGN PATENT DOCUMENTS

| | | |
|---|---|---|
| 0 225 177 | 11/1986 | European Pat. Off. . |
| 0 278 355 | 2/1988 | European Pat. Off. . |
| 0 293793 | 5/1988 | European Pat. Off. . |
| 0 304311 | 8/1988 | European Pat. Off. . |
| 0 353 188 | 7/1989 | European Pat. Off. . |
| 0 509841 | 4/1992 | European Pat. Off. . |
| 0 510 658 | 4/1992 | European Pat. Off. . |
| WO 87/04462 | 7/1987 | WIPO . |
| WO 89/12681 | 12/1989 | WIPO . |
| WO 93/24635 | 12/1993 | WIPO . |
| WO 93/25676 | 12/1993 | WIPO . |
| WO 94/08012 | 4/1994 | WIPO . |
| WO 96/14422 | 5/1996 | WIPO . |
| WO 97/38123 | 10/1997 | WIPO . |
| WO 98/18946 | 5/1998 | WIPO . |

OTHER PUBLICATIONS

Keyt, B. et al., Proc. Natl. Acad. Sci. USA, vol. 91, pp. 3670–3674, Apr. 1994.

Lunn, C. et al., Meth. Enzymol., vol. 125, pp. 138–149, 1986.

Anderson, S. et al., Proc. Natl. Acad. Sci. USA, vol. 80, pp. 6838–6842, 1983.

Anderson et al., "A new *Escherichia coli* gene, dsbG, encodes a periplasmic protein involved in disulphide bond formation, required for recycling DsbA/DsbB and DsbC redox proteins," *Mol. Microbiol.*, 26(1):121–132, 1997.

Anderson et al., "A new *Escherichia coli* gene, dsbG, encodes a periplasmic protein involved in disulphide bond formation, required for recycling DsbA/DsbB and DsbC redox proteins," submitted to the EMBL/GenBank/DDBJ database Accession No. AF000956. May 13, 1997.

International Search Report dated Jan. 27, 1999 (PCT/US98/12004) (UTFB:667P).

van Straaten et al., "The functional properties of DsbG, a thiol–disulfide oxidoreductase from the periplasm of *Escherichia coli,*" *FEBS Letters*, 428:255–258, 1998.

International Search Report dated Jul. 9, 1997 (UTFB:632P—).

Bardwell et al., "The bonds that tie: Catalyzed disulfide bond formation," *Cell,* 74:769–771, 1993.

Bardwell et al., "A pathway for disulfide bond formation in vivo," *Proc. Natl. Acad. Sci. USA,* 90:1038–1042, 1993.

Bardwell et al., "Identification of a protein required for disulfide bond formation in vivo," *Cell,* 67:581–589, 1991.

Bardwell, "Building bridges: Disulphide bond formation in the cell," *Mol. Microbiol.,* 14(2):199–205, 1994.

Bulleid, "Protein disulfide–isomerase: Role in biosynthesis of secretory proteins," *Adv. Prot. Chem.,* 44:125–150, 1993.

Cai et al., "Chaperone–like activity of protein disulfide isomerase in the refolding of a protein with no disulfide bonds," *J. Biol. Chem.,* 269(40):24550–24552, 1994.

Creighton et al., "Kinetic Role of a meta–stable native–like two–disulfide species in the folding transition of bovine pancreatic trypsin inhibitor," *J. Mol. Biol.,* 179:497–526, 1984.

Creighton et al., "On the biosynthesis of bovine pancreatic trypsin inhibitor (BPTI)," *J. Mol. Biol.,* 232:1176–1196, 1993.

Creighton, "Catalysis by protein–disulphide isomerase of the unfolding and refolding of proteins with disulphide bonds," *J. Mol. Biol.,* 142:43–62, 1980.

(List continued on next page.)

*Primary Examiner*—Charles L. Patterson, Jr.
*Assistant Examiner*—Peter P. Tung
*Attorney, Agent, or Firm*—Arnold, White & Durkee

[57] ABSTRACT

Disclosed are methods and compositions for producing heterologous disulfide bond containing polypeptides in bacterial cells. In preferred embodiments the methods involve co-expression of a prokaryotic disulfide isomerase, such as DsbC or DsbG and a gene encoding a recombinant eukaryotic polypeptide. Exemplary polypeptides disclosed include tissue plasminogen activator.

46 Claims, 3 Drawing Sheets

OTHER PUBLICATIONS

Dailey et al., "Mutants in disulfide bond formation that disrupt flagellar assembly in *Escherichia coli*," *Proc. Natl. Acad. Sci. USA*, 90:1043–1047, 1993.

Darby et al., "Dissecting the mechanism of protein disulfide isomerase: catalysis of disulfide bond formation in a model peptide," *Biochemistry*, 33:7937–7947, 1994.

De Sutter et al., "Production of enzymatically active rat protein disulfide isomerase in *Escherichia coli*," *Gene*, 141:163–170, 1994.

De Sutter et al., "Disulphide bridge formation in the periplasm of *Escherichia coli*: β–lactamase::human IgG3 hinge fusions as a model system," Mol. *Micro.*, 6(15):2201–2208, 1992.

Freedman et al., "Protein disulphide isomerase: Building bridges in protein folding," *TIBS*, 19:331–336, 1994.

Freedman et al., "Role of protein disulphide isomerase in the expression of native proteins," *Biochem. Soc. Symp.*, 55:167–192, 1994.

Fukuzono et al., Production of Biologically Active Mature Brain–derived Neurotrophic Factor in *escherichia coli*, Biosci. Biotech. Biochem., 59(9):1727–1731, 1995.

Georgiou and Valax, "Expression of correctly folded proteins in *escherichia coli*," Current Opinion in Biotechnology, 7:190–197, 1996.

Goldenberg, "Native and non–native intermediates in the BPTI folding pathway," *TIBS*, 17:257–261, 1992.

Grauschopf et al., "Why is DsbA such an oxidizing disulfide catalyst?," *Cell*, 83:947–955, 1995.

Grunfeld et al., "Effector–assisted refolding of recombinant tissue–plasminogen activator produced in *Escherichia coli*," *Appl. Biochem. Biotechnol.*, 33:117–38, 1992.

Guilhot et al., "Evidence that the pathway of disulfide bond formation in *Escherichia coli* involves interactions between the cysteines of DsbB and DsbA," *Pro. Natl. Acad. Sci. USA*, 92:9895–9899, 1995.

Hockney, "Recent developments in heterologous protein production in *Escherichia coli*," *Trends Biotech.*, 12:456–463, 1994.

Hwang et al., "Oxidized Redox State of Glutathione in the Endoplasmic Reticulum," *Science*, 257:1496–1502, 1992.

Jander et al., "Two cysteines in each periplasmic domain of the membrane protein DsbB are required for its function in protein disulfide bond formation," *EMBO J.*, 13(21):5121–5127, 1994.

Joly et al., Protein Folding Activities of *Escherichia coli* Protein Disulfide Isomerase, *Biochemistry*, 33:4231–4236, 1994.

Kamitani et al., "Identification and characterization of an *Escherichia coli* gene required for the formation of correctly folded alkaline phosphatase, a periplasmic enzyme," *EMBO J.*, 11(1);57–62, 1992.

Kishigami et al., "Redox states of DsbA in the periplasm of *Escherichia coli*," FEBS *Letters*, 364:55–58, 1995.

Knappik et al., "The effect of folding catalysts on the in vivo folding process of different antibody fragments expressed in *Escherichia coli*," *Bio/Technology*, 11(1):77–83, 1993.

LaMantia et al., "The essential function of yeast protein disulfide isomerase does not reside in its isomerase activity," *Cell*, 74:899–908, 1993.

Lyles et al., "Mutations in the thioredoxin sites of protein disulfide isomerase reveal functional nonequivalence of the N– and C–terminal domains," *J. Biol. Chem.*, 269:30946–309523, 1994.

Marks et al., "Production of native, correctly folded bovine pancreatic trypsin inhibitor by *Escherichia coli*," *J. Biol. Chem.*, 261(16):7115–7118, 1986.

Martin et al., "Crystal structure of the DsbA protein required for disulphide bond formation in vivo," *Nature*, 365:464–468, 1993.

McGrath et al., "The Sequence and Reactive Site of Ecotin," *J. Biol. Chem.*, 266(10):6620–6625, 1991.

Missiakas et al., "Identification and characterization of a new disulfide isomerase–like protein (DsbD) in *Escherichia coli*," *EMBO J.*, 14(14):3415–3424, 1995.

Missiakas et al., "Identification and characterization of the *Escherichia coli* gene dsbB, whose product is involved in the formation of disulfide bonds In vivo," *Proc. Natl. Acad. Sci. USA*, 90:7084–7088, 1993.

Missiakas et al., "The *Escherichia coli* dsbC (xprA) gene encodes a periplasmic protein involved in disulfide bond formation," *EMBO J.*, 13(8):2013–2020, 1994.

Nilsson et al., "Secretion incompetence of bovine pancreatic trypsin inhibitor expressed in *Escherichia coli*," *J. Biol. Chem.*, 266(5):2970–2977, 1991.

Noiva et al., "Protein Disulfide Isomerase," *J. Biol. Chem.*, 267(6):3553–3556, 1992.

Noiva et al., "Peptide binding by protein disulfide isomerase, a resident protein of the endoplasmic reticulum lumen," *J. Biol. Chem.*, 266(29):19645–19649, 1991.

Ostermeier et al., "The Folding of bovine pancreatic trypsin inhibitor in the *Escherichia coli* periplasm," *J. Biol. Chem.*, 269(33):21072–21077, 1994.

Ostermeier et al., "Eukaryotic protein disulfide isomerase complements *Escherichia coli* dsbA mutants and increases the yield of heterologous secreted protein with disulfide bonds," *J. Biol. Chem.*, 271(18):10616–10622, 1996.

Pollitt et al., "Role of primary structure and disulfide bond formation in β–lactamase secretion." *J. Bacteriol.*, 153(1):27–32, 1983.

Puig et al., "Anti–chaperone behavior of BiP during the protein disulfide isomerase–catalyzed refolding of reduced denatured lysozyme," *J. Biol. Chem.*, 269(41):25889–25896, 1994.

Puig et al., "Protein disulfide isomerase exhibits chaperone and anti–chaperone activity in the oxidative refolding of lysozyme," *J. Biol. Chem.*, 269(10):7746–7771, 1994.

Puig et al., "The role of the thiol/disulfide centers and peptide binding site in the chaperone and anti–chaperone activities of protein disulfide isomerase," *J. Biol. Chem.* 269:19128–19135, 1994.

Rijken and Groeneveld, "Isolation and Functional Characterization of the Heavy and Light Chains of Human Tissue––Type Plasminogen Activator," J. Biol. Chem., 26(7):3098–3102, 1986.

Rudolph et al., "In vitro folding of inclusion body proteins," *FASEB J*, 10:49–56, 1996.

Shevchik et al., "Characterization of DsbC, a periplasmic protein of *Erwinia chrysanthemi* and *Escherichia coli* with disulfide isomerase activity," *EMBO J.*, 13(8):2007–2012, 1994.

Simmons et al., "Translational level is a critical factor for the secretion of heterologous proteins in *Escherichia coli*," *Nature Biotechnology*, 14:626–634, 1996.

van Mierlo et al., "Partially folded conformation of the (30–51) intermediate in the disulphide folding pathway of bovine pancreatic trypsin inhibitor," *J. Mol. Biol.*, 229:1125–1146, 1993.

Waldenström et al., "Synthesis and secretion of a fibrinolytically active–type plasminogen activator variant in *Escherichia coli*," *Gene*, 99:243–248, 1991.

Walker et al., "Effect of redox environment on the in vitro and in vivo folding of RTEM–1 β–Lactamase and *Escherichia coli* alkaline phosphatase," *J. Biol. Chem.*, 269(45):28487–28493, 1994.

Weissman et al. "Efficient catalysis of disulphide bond rearrangements by protein disulphide isomerase," *Nature*, 365:185–188, 1993.

Weissman et al. "Kinetic role of nonnative species in the folding of bovine pancreatic trypsin inhibitor," *Proc. Natl. Acad. Sci. USA*, 89:9900–9904, 1992.

Weissman et al. "Reexamination of the folding of BPTI: predominance of native intermediates," *Science*, 253:1386–1393, 1991.

Wittrup, Disulfide Bond Formation and Eukaryotic Secretory Productivity, Current Opinion in Biotechnology, 6:203–208, 1995.

Wülfing et al., "Correctly folded T–cell receptor fragments in the periplasm of *Escherichia coli*," *J. Mol. Biol.*, 242:655–669, 1994.

Wülfing et al., "Protein folding in the periplasm of *Escherichia coli*," *Mol. Microbiol.*, 12(5):685–692, 1994.

Wunderlich et al., "Bacterial protein disulfide isomerase: efficient catalysis of oxidative protein folding at acidic pH," *Biochemistry*, 32:12251–12256, 1993.

Wunderlich et al., "Redox properties of protein disulfide isomerase (DsbA) from *Escherichia coli*," *Protein Sci.*, 2:717–726, 1993.

Wunderlich et al., "In vivo control of redox potential during protein folding catalyzed by bacterial protein disulfide–isomerase (DsbA)," *J. Biol. Chem.*, 268(33):24547–24550, 1993.

Zapun et al., "Effects of DsbA on the disulfide folding a bovine pancreatic trypsin inhibitor and α–Lactalbumin," *Biochemistry*, 33:5202–5211, 1994.

Zapun et al., "Folding in vitro of bovine pancreatic trypsin inhibitor in the presence of proteins of the endoplasmic reticulum," *Proteins: Structure, Function, and Genetics*, 14:10–15, 1992.

Zapun et al., "Replacement of the active–site cysteine residues of DsbA, a protein required for disulfide bond formation in vivo," *Biochemistry*, 33:1907–1914, 1994.

Zapun et al., "The reactive and destabilizing disulfide bond of DsbA, a protein required for protein disulfide bond formation in vivo," *Biochemistry*, 32:5083–5092, 1993.

METHODS FOR PRODUCING HETEROLOGOUS DISULFIDE BOND-CONTAINING POLYPEPTIDES IN BACTERIAL CELLS

The United States government has certain rights in the present invention pursuant to Grant 1R01-GM47520-01A1 from the National Institutes of Health.

1. BACKGROUND OF THE INVENTION

1.1 Field of Invention

The present invention relates generally to the field of molecular biology. More particularly, certain embodiments concern methods and compositions for the bacterial production of heterologous disulfide bond-containing polypeptides. In a preferred embodiment the eukaryotic protein, tissue plasminogen activator (tPA), and variants thereof, are produced in *E. coli* cells using recombinant vectors which direct the coexpression of these proteins with a prokaryotic enzyme, such as DsbC or DsbG.

1.2 Description of the Related Art

1.2.1 Protein Expression in Bacterial Hosts

A significant achievement in molecular biology has been the use of recombinant bacterial cells to produce eukaryotic proteins. This method has been particularly useful for production of medically important polypeptides that are obtained in low yield from natural sources. Often otherwise difficult to obtain in quantity, such proteins are "overexpressed" in the host cell and subsequently isolated and purified. Preinsulin for example may be produced in a recombinant prokaryotic microorganism carrying DNA encoding rat preinsulin (U.S. Pat. Nos. 4,431,740 and 4,652,525, each specifically incorporated herein by reference).

Expression of multiple disulfide bond-containing eukaryotic polypeptides, and particularly mammalian proteins, in bacterial cells has frequently produced disappointing and unsatisfactory results because conditions and environment in the host cells were not conducive to correct folding. Disulfide bond formation is a process mainly restricted to proteins outside the cytoplasmic compartment such as those secreted into the lumen of the endoplasmic reticulum (ER) or the periplasm of gram negative bacteria. Correct folding may depend on the formation of cysteine-cysteine linkages and subsequent stabilization of the protein into an enzymatically active structure. However, the cytoplasm is in fact a reducing environment due to the presence of thioredoxin reductase or reduced glutathione, thus blocking oxidation so that disulfide bonds do not form. The endoplasmic reticulum (ER) apparently is more conducive to oxidation due to the presence of oxygen or oxidized glutathione.

Recent studies indicate that disulfide bond formation in vivo is a catalyzed process, either in the ER or periplasm. In *E. coli*, a pathway for the formation of disulfide bonds in secreted proteins has been described, involving two proteins, DsbA and DsbB (Bardwell et al., 1993a; 1993b; Missiakas et al., 1993).

A role for these Dsb proteins is supported by the observation that mutants of *E. coli* that lack DsbA or DsbB are defective with respect to disulfide bond formation (Dailey and Berg, 1993). In the yeast *Saccharomyces cerevisiae*, a similar defect is found in certain mutants defective in protein disulfide isomerase (PDI) gene. Disulfide bond formation in carboxypeptidase Y in these mutants is impaired.

1.2.2 Recombinant Expression of Eukaryotic Proteins in Bacterial Hosts

It is known that disulfide bonds are critical in some proteins in order for proper folding and even in transport and secretion. Yet many proteins cannot be efficiently expressed in bacterial hosts due to failure of disulfide bond formation. Cytoplasmic expression systems in bacteria are not conducive to disulfide bond formation because of a reducing environment. The presence of proteases in the cytoplasm may cause rapid degradation of the protein, resulting in low yields.

1.2.3 Protein Folding in Vitro and in Vivo

Much research has been conducted in the field of protein folding showing that, in vitro, reduced and denatured ribonuclease could refold into the active enzyme with the formation of suitable disulfide bonds. Later, a catalyst responsible for oxidative folding in eukaryotes was discovered, called protein disulfide isomerase (PDI).

Two types of proteins that assist in protein folding have been described: non-catalytic molecular chaperones that presumably prevent improper interactions leading to aggregation and events other than proper folding, and catalysts for two steps in protein folding, cis-trans prolyl isomerization and disulfide bond formation. While clear evidence for an in vivo requirement of prolyl isomerase activity is still lacking, the relatively recent isolation of mutants that are severely defective in disulfide bond formation has confirmed that this latter folding step is catalyzed in vivo.

U.S. Pat. Nos. 5,270,181 and 5,292,646 (specifically incorporated herein by reference in their entirety) disclose recombinant production of heterologous proteins by expression as a fusion protein with a thioredoxin-like protein (such as the thioredoxin-like domain of PDI) for high stability and solubility. Jap. Pat. Appl. No. JP 60-38771 discloses the expression of a human PDI gene linked to human serum albumin pre-pro sequence and co-expression of this linked gene and a foreign gene encoding a polypeptide. Intl. Pat. Appl. Publ. No. WO 93/25676 discloses the production of disulfide-bonded recombinant proteins using a PDI, preferably a yeast PDI. Eur. Pat. Appl. No. EP 293,793 discloses a polypeptide with PDI activity ensuring natural disulfide bridge arrangement in recombinant proteins. Intl. Pat. Appl. Publ. No. WO 94/08012 discloses increasing secretion of over-expressed gene products by co-expression of a chaperone protein such as a heat-shock protein or PDI. Eur. Pat. Appl. No. EP 509,841 discloses increased secretion of human serum albumin from yeast cells using a co-expression system involving PDI and a protein.

The formation of disulfide bonds is essential for the correct folding and stability of numerous eukaryotic proteins of importance to the pharmaceutical and bioprocessing industries. However, numerous studies over the last fifteen years have demonstrated that, with few exceptions, multidisulfide proteins cannot be expressed in active form in bacteria. The production of technologically important proteins with four or more disulfides is costly and complicated and has to rely either on expression of higher eukaryotes that provide a favorable environment for the formation of disulfide bonds or refolding from inclusion bodies (Hockney, 1994; Georgiou and Valax, 1996).

1.2.4 Deficiencies in the Prior Art

Currently there is a lack of efficient methods of producing complex eukaryotic proteins with multiple disulfide bonds on an economic scale. Likewise, there is a need to develop methods which produce proteins that are correctly folded and active without the need for reactivation or subsequent processing once isolated from a host cell.

Therefore, what is lacking in the prior art are methods, recombinant vectors, host cells, and compositions comprising high-level expression of eukaryotic disulfide bond-containing polypeptides (such as trypsin inhibitor, tPA, and variants thereof) which are soluble, correctly-folded, biologically-active, and readily-isolatable from cell extracts of prokaryotic hosts. In particular there is a need to produce tPA and variants thereof which are biologically active, correctly-folded, and localized to the soluble fraction of bacterial cells.

2. SUMMARY OF THE INVENTION

The present invention overcomes one or more of these and other drawbacks inherent in the prior art by providing novel methods, recombinant host cells, vectors and compositions resulting therefrom for efficiently producing eukaryotic polypeptides containing disulfide bonds in bacterial host cells which are active, correctly folded, and secreted from the bacterial cell to provide economic and convenient means for the recovery, isolation, and purification of the recombinant polypeptide of interest. The present invention represents a significant breakthrough in the fields of molecular biology, protein chemistry, and pharmaceutics, in producing eukaryotic recombinant polypeptides in prokaryotic hosts through novel methods and recombinant vectors which direct the expression of eukaryotic polypeptides of interest using an E. coli host cell which also expresses DsbC or DsbG. Recovery of correctly folded, active, soluble recombinant polypeptides in significant quantity is now possible by employing the disclosed methods and compositions.

Accordingly, in one aspect the present invention provides a process for producing a heterologous polypeptide in bacteria. The process generally comprises culturing bacterial cells, which contain a nucleic acid segment encoding a DsbC or DsbG protein, a nucleic acid segment encoding a heterologous polypeptide, a signal sequence for secretion of the DsbC or DsbG protein and the heterologous polypeptide, and an inducible promoter for both nucleic acid segments under conditions effective to facilitate secretion of both the heterologous polypeptide and the DsbC or DsbG protein into the periplasm of the cells or into the medium in which the bacterial cells are cultured, and then recovering the heterologous polypeptide from the periplasm or the culture medium.

The over-expression and secretion of the bacterial DsbC or DsbG protein results in a significant increase in the amount of heterologous polypeptide produced in the periplasm of bacteria or in the culture medium. In the specific example shown below, the over-expression and secretion of the E. coli protein DsbC resulted in a large increase in the total yield of active human tPA produced in the soluble fraction of the periplasmic space of E. coli. Furthermore, this total yield increase is accomplished by culturing in the absence of any glutathione in the medium and without co-expressing or over-expressing the E. coli heat-shock transcription factor, RpoH.

It is understood that the invention provides a method of providing biologically active polypeptides that are characterized as having multiple disulfide bonds. In using the term "biologically active" one recognizes that the natural activity of such molecules depends on several factors, including proper folding of the protein chain. Folding of course may be altered in many ways and may result in improperly folded molecules that lack normal biological activity or have significantly altered activity. As used herein, the biologically active molecules generated by the disclosed methods are typically those with 4 or more disulfide bonds, ranging up to 12, 14, or even 17, or more, and which form from specific orientations to promote correct folding of the native protein. Multiple disulfide bonds resulting from improper orientation of nascently formed proteins in the cell lead to misfolding and loss or absence of biological activity. Thus, a biologically-active polypeptide containing multiple disulfide bonds will be correctly folded; disulfide bonds will form to provide a tertiary and where applicable, quarternary structure leading to a molecule with native functional activity with respect to substrates and/or catalytic properties.

The method further provides biologically active, soluble polypeptides that contain multiple disulfide bonds. As used herein, soluble is intended to encompass polypeptides that are expressed in bacterial cells in soluble form, rather than in an insoluble matrix such as inclusion bodies. While such soluble polypeptides are generally expressed in the periplasm, secretion outside the cell may also be envisioned. Leaky cell membranes, for example, can be engineered for host cells by methods known to those skilled in the art.

There are numerous advantages in employing systems that allow expression of proteins in a soluble fraction. A significant number of polypeptides with multiple disulfide bonds are not normally expressed in the soluble cell fraction; tPA for example is currently produced in bacteria inclusion bodies. Purification methods are cumbersome and require refolding procedures that so far have resulted in only low yields of biologically active material. In typical procedures, proteins are released from inclusion bodies using a variety of chaotropic agents such as detergent or protein denaturants, e.g., urea, then isolated and refolded by employing reducing agents such as glutathione, dithioerythritol, dithiothreitol, or other suitable reducing agent. Generally, refolding results in low yields of biologically active material.

An important feature of the present invention is the production of multiple disulfide bond-containing polypeptides such as tPA which have typically been isolated in an insoluble inactive form. The tPA produced in accordance with the disclosed procedures provides a more active protein that is conveniently isolated from the soluble cell fraction. The soluble, active tPA produced by this method does not require extensive purification. More particularly, there is no need for solubilization and refolding procedures. Salts, detergents and/or reducing agents are unnecessary. Recovery of tPA from bacterial cells, by the methods herein disclosed, provides a biologically active molecule with higher specific activity than recombinant tPA produced by current methods. Intl. Pat. Appl. Publ. No. WO 96/14422 discloses the recombinant expression of eukaryotic proteins when co-expressed with DsbA or DsbC. A limitation of the prior art (i.e. the production of unfolded, biologically inactive, inclusion body constrained proteins) is overcome by the methods and compositions of the present invention. Such improvement facilitates the recovery of intact, biologically active soluble protein directly, and obviates the need for additional modification, activation, or solubilization.

It is recognized that the disclosed methods of the present invention have been illustrated for the expression of recombinant multiple disulfide bond containing polypeptides in bacterial cells and particularly in E. coli cells. As such, the resulting recombinant protein will not be glycosylated. However, where glycosylation is desired, chemical or genetic engineering methods known to those of skill in the art may be readily applied to modify the proteins obtained by the disclosed methods and expression systems, to provide partially- or fully-glycosylated protein products.

While the methods and expression systems have been demonstrated with tissue plasminogen activator, it will be understood that such methods will apply equally well to a wide range of mutants of tPA or to the expression of other multiple disulfide bond-containing polypeptide mutants and analogs. It may be desirable, for example, to develop mutants that will lead to increased yields while retaining the full biological activity that the disclosed method preserves. Likewise, it is expected that variants and mutants of these molecules may also be readily isolated from the soluble fraction of bacterial cells in biologically-active form.

In a general aspect, the invention is the production of biologically active, recombinant eukaryotic polypeptides that in their active form contain multiple disulfide bonds. In preferred embodiments, the proteins produced using the methods of the present invention have four or more disulfide bonds. In particular embodiments the polypeptide will have 4, 5, 6, 7, 8, 9, 10, 11, 12, 13, 14, 15, 16, or 17, or even more disulfide bonds. The formation of disulfide bonds in such a eukaryotic protein permits the correct folding, proper conformation, and/or tertiary structure of the polypeptide to form, thereby resulting in a structurally-correct, and/or biologically-active protein. As such, when conformationally correct, the eukaryotic protein prepared as disclosed, may exhibit its native shape, structure, and/or activity, and in the case of an enzyme, may possess the same or comparable specific activity toward its particular substrate(s) as if the protein were produced in its native eukaryotic environment.

The method of production involves expression in a bacterial cell of a DNA segment encoding DsbC or DsbG protein operatively linked to a signal sequence and a second DNA encoding the recombinant polypeptide that has the multiple disulfide bonds.

A preferred embodiment is use of the described method to produce biologically active, recombinant tPA. More preferably the tPA is human tPA. Where expression occurs in an *E. coli* cell, the DsbC or DsbG protein is preferably an *E. coli* DsbC or DsbG protein, or a DsbC or DsbG protein of other bacterial origin. Preferred signal sequences in coliform and salmonella cells include OmpA, Lpp, LamB, MalE, PelB, and StII. While use of different promoters is contemplated, including among others the lac-lpp, tac, tet, trc, phoA, lpp, T7, $\lambda_{PL}$, and $P_{BAD}$, a preferred promoter is lac-lpp.

In other embodiments, the invention includes an expression system capable of expressing a DsbC or DsbG protein and a eukaryotic protein having multiple disulfide bonds, preferably about four or more and up to about 18 or more. However, it is contemplated that the system will allow expression of biologically active multiple disulfide bond containing polypeptides in bacterial cells even where more than 18 disulfide bonds are part of the active molecule, such as multimers where internal and chain or oligomer forming bonds are present.

The expression system may include a first expression unit containing a DNA segment comprising a disulfide isomerase operatively linked to a signal sequence and a second expression unit comprising a DNA segment encoding a recombinant polypeptide having at least about four disulfide bonds operatively linked to a signal sequence. The expression units may be separate recombinant vectors or included within a single recombinant vector. In either case, the recombinant vectors will be capable of expression in a single bacterial cell.

2.1 Methods for Producing Recombinant Polypeptides Having Multiple Disulfide Bonds in Bacterial Cells The present invention discloses methods for producing recombinant multi-disulfide polypeptides such as tPA, including human tPA, tPA derivatives, and tPA fusion proteins; antibody fragments; protease inhibitors; therapeutic enzymes; lymphokines; neurotrophic factors; and related polypeptides and derivatives; mutants; and fusion proteins derived therefrom. One of the problems with tPA isolated from natural sources is low yields and extensive purification processes. The present invention in an important embodiment illustrates a strategy for overproducing tPA from a bacterial host, employing DNA constructs encoding human tPA and *E. coli* DsbC or DsbG to transform Gram-negative bacterial cells and coexpress the two proteins to produce active, soluble, secreted recombinant tPA polypeptides in vivo. In addition to the production of the complete tPA molecule, derivatives of tPA lacking the finger-like region, one or both of the kringle sub-domains or the epidermal growth factor subdomain may also be expressed in functional form. Such mutants as well as mutated tPA molecules with amino acid substitutions that affect the proteolytic activity exhibit useful pharmacological and/or pharmacokinetic properties, and are all contemplated to fall within the scope of the present invention.

2.2 Methods for Producing Biologically-Active Eukaryotic Polypeptides in Bacteria In an important embodiment the invention concerns a method of producing in a prokaryotic host cell a biologically-active, eukaryotic polypeptide having four or more disulfide bonds. The method involves co-expressing in a suitable prokaryotic cell, such as a bacterial cell, a DNA segment encoding a prokaryotic signal sequence-eukaryotic disulfide isomerase fusion protein and a DNA segment encoding a prokaryotic signal sequence-eukaryotic recombinant polypeptide fusion protein under suitable physiological conditions to produce the recombinant eukaryotic fusion protein of interest. It is contemplated that the fusion protein of interest may be any eukaryotic protein for which expression in a prokaryotic host is desirable, but in particular, eukaryotic proteins which contain four or more disulfide bonds, and preferably those which contain at least four or five disulfide bonds, six or seven bonds, 8, 9 or 10 bonds, even those proteins having 11, 12, 13, 14, 15, 16, 17, 18 or more disulfide bonds.

The signal sequence employed in the practice of the invention may be any such sequence which encodes a signal capable of directing the export of the fusion protein to the bacterial periplasm or outer membrane, or alternatively into the culture supernatant in which such cells are grown. Typically, the signal sequence, or leader peptide, may be any of those well-known to those of skill in the art to be capable of directing the export of proteins in vivo in bacterial cells. A particularly preferred sequence is the *E. coli* alkaline phosphatase (PhoA) OmpA signal sequence, but equally preferred signal sequences include the Lpp, LamB, MalE, PelB or StII signal sequences and the like.

2.3 Expression Systems for the Production of Eukaryotic Polypeptides Bacteria

In another preferred embodiment, the invention concerns an expression system that expresses in a prokaryotic host cell a gene encoding a DsbC or DsbG protein, and a gene encoding an eukaryotic polypeptide having four or more disulfide bonds. Preferably the protein is a heterologous protein. An exemplary expression system is one that is useful in the expression of recombinant eukaryotic polypeptides having four or more disulfide bonds, even up to and including those having fourteen, fifteen, sixteen, seventeen, or eighteen or more disulfide bonds.

The expression system in a general sense is composed of two expression units: one containing a DNA segment which encodes a disulfide isomerase protein, and preferably a disulfide isomerase fusion protein, and a second unit containing a DNA segment which encodes the recombinant fusion protein of interest. The two expression units may either be contained on a single recombinant vector, or alternatively, may each be contained on two separate and distinct recombinant vectors. In the case of the latter, any two recombinant vectors may be utilized so long as the replicons are compatible in the same host cell and that the expression unit of each vector functions in the same cell to permit the co-expression of the two expression units. In an illustrative embodiment described in Section 5, the inventors have demonstrated the coexpression of pLPPsOmpArPDI and pACYCBPTI to be particularly useful in the production of BPTI from bacterial host cells, and the coexpression of DsbC or DsbG and a recombinant gene encoding tPA to be particularly useful in the production of tPA from bacterial host cells.

Expression of the fusion proteins may be promoted by any of a number of suitable promoter sequences which are well-known to promote the transcription of genes and/or operons in bacterial cells. In preferred embodiments, the DNA segments of the present invention are expressed from a lac, ara, lac-lpp, tet, tac, trc, phoA $P_{BAD}$, $\lambda_{PL}$, lpp, or T7 promoter. The components of the expression system described herein may be located on separate recombinant vectors with each transcriptional unit under the control of its own promoter, or alternatively, the components of the expression system may be located within a single recombinant vector. In the latter case, the disulfide isomerase-encoding transcriptional unit may be controlled by one promoter, while the recombinant disulfide bond-containing polypeptide-encoding transcriptional unit may be controlled by a separate promoter, or alternatively, the two transcriptional units may be in the form of a "tandem" transcriptional unit with both being controlled by a single promoter located 5' of both coding regions. The inventors have found the lac-lpp promoter to be particularly useful in the practice of the present invention.

2.4 Recombinant Host Cells

In particular, the invention provides recombinant Gram-negative host cells, preferably Emterobacteraceae cells such as those from the genera *Escherichia Salmonella*, transformed with nucleic acid segments encoding eukaryotic disulfide bond-containing polypeptides and DsbC or DsbG from which the correctly-folded, biologically-active disulfide bond-containing polypeptide may be isolated. In sharp contrast to native un-engineered host cells, these transformed host cells have the ability to catalyze the formation and isomerization of disulfide bonds in eukaryotic proteins.

In a preferred embodiment, *E. coli* cell lines such as such as SF103, SF110, UT5600, RB791, R189, MC9100, and JCB570, as well as others described in U.S. Pat. No. 5,508,192 are particularly preferred.

A host cell was deposited on Mar. 28, 1997 with the American Type Culture Collection, 10801 University Boulevard, Manassas, Va. 20110-2209 in accordance with U.S. Patent and Trademark Office requirements for microorganism deposits, and assigned the following accession number: ATCC 98380. The deposit has been made in accordance with the terms of the Budapest Treaty on the international recognition of the deposit of microorganisms for the purposes of patent procedure. In accordance with the terms of the Budapest Treaty: (a) the deposit will be made accessible to the Commissioner upon request during the pendency of this application; (b) all restrictions to access by the public of this deposit will be irrevocably removed upon granting of the patent; (c) this deposit will be maintained in the public depository for a period of thirty years or five years after the last request, or for the effective life of the patent, whichever is longer; and, (d) this deposit will be replaced if it should ever become non-viable.

In addition to the cell lines described above, other prokaryotic hosts may also be used in the practice of the present invention. These organisms include *E. coli* strain SF103, RR1, LE392, B, $\chi^{1776}$ (ATCC 31537) as well as *E. coli* W3110 (F⁻, k⁻, prototrophic, ATCC 273325). Enterobacteriaceae species such as *Salmonella typhimurium* and *Serratia marcescens*, and various Pseudomonas species may also be used.

2.5 Recombinant Vectors for Expressing Eukaryotic Proteins in Prokaryotic Hosts P In a related embodiment, the invention discloses a recombinant vector comprising a first transcriptional unit encoding an *E. coli* DsbC or DsbG protein operatively linked to a signal sequence and a second transcriptional unit comprising a DNA segment encoding a mammalian disulfide bond containing protein, such as tPA or PTI.

A preferred plasmid for cloning the eukaryotic "target" polypeptide-encoding DNA fragment is pACYC184, although any other vector which may be maintained in the bacterial host and is compatible with the vector expressing the isomerase may also be used (e.g., pACYC177, p15, pSC101). In an illustrative embodiment, pACYC184 was used to create pACYCBPTI and ptPA177 which contain DNA sequences encoding bovine PTI and human tPA, respectively.

A preferred plasmid for the expression of a DsbC or DsbG transcriptional unit is pTrc99A (see below).

2.6 Isolation of Soluble Heterologous Proteins from Bacterial Cells

Another aspect of the invention concerns the isolation of biologically-active recombinant eukaryotic disulfide bond-containing polypeptides from the soluble fraction of bacterial cells.

The inventors have demonstrated that methods described herein may result in secretion of a soluble form of the recombinant fusion polypeptides to the bacterial periplasmic space. It is also contemplated that particular gene constructs may be utilized which alternatively direct the export of the fusion proteins of interest to either the outer membrane or even result in the secretion of the fusion proteins to the culture supernatant, from which the particular polypeptides may be isolated using conventional techniques for the isolation and purification of proteins.

2.7 Purification of Biologically-Active Eukaryotic Proteins from Bacteria

Because wild-type prokaryotic hosts lack the appropriate enzymes to perform isomerization, and because native bacteria cannot secrete properly folded and active forms of eukaryotic polypeptides, a significant limitation in the purification of valuable recombinant proteins has existed. The present invention, however, overcomes limitations in the art by providing recombinant host cells which produce correctly-folded, biologically-active eukaryotic proteins in soluble, secreted form.

The recombinant proteins of the present invention may contain multiple disulfide bonds. Particularly preferred are proteins which contain at least four disulfide bonds or more. The inventors have demonstrated success with the method expressing proteins having four disulfide bonds (such as PTI), and surprisingly have demonstrated success with proteins having 17 disulfide bonds, such as mammalian tPA.

In preferred embodiments, the novel methods disclosed herein have employed bacterial cells such as *E. coli* to produce high yields of multi-disulfide bond-containing eukaryotic enzymes. For example, the inventors have succeeded in producing significant quantities of active, correctly folded tPA in a bacterial cell. This protein has 17 disulfide bonds that must form correctly in order for the protein to be active. The invention is the first demonstration of production of significant quantities of tPA from bacterial host cells which is not associated with insoluble intracellular inclusion bodies. Likewise, the invention has been used to facilitate the production of another commercially important enzyme, pancreatic trypsin inhibitor, and in particular, bovine PTI, using bacterial hosts which overexpress DsbC or DsbG. The invention represents a breakthrough in the production of commercial quantities of such multi-disulfide bond-containing proteins of economic interest by providing rapid, inexpensive methodologies for secretion of such proteins by the engineered bacterial cells.

2.8 Nucleic Acid Segments Encoding Peptides of Interest

The process of selecting and preparing a nucleic acid segment which includes the preferred nucleic acid sequences encoding the peptides of interest is well-known to those of skill in the art. This may alternatively be described as preparing a nucleic acid fragment, or cloning a specific gene. Of course, fragments may also be obtained by other techniques such as, e.g., by mechanical shearing or by restriction enzyme digestion. Small nucleic acid segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. Nos. 4,683,195 and 4,683,202 (each specifically incorporated herein by reference), by introducing selected sequences into recombinant vectors for recombinant production, and by other recombinant DNA techniques generally known to those of skill in the art of molecular biology.

2.9 Heterologous Protein Compositions

The invention also relates to compositions comprising a biologically-active, tissue plasminogen activator operatively linked to a bacterial export signal peptide.

Using the methods disclosed herein, the inventors have developed novel compositions comprising tissue plasminogen activator operatively linked to a bacterial export signal peptide which has a specific activity of 5–30 g/L/OD$_{600}$ unit of protein The tPA composition is both soluble and biologically-active, and is isolatable from the bacterial periplasm.

The proteins of the invention may be prepared using an expression system which directs the recombinant expression of the eukaryotic polypeptides of eukaryotic polypeptides. The engineering of DNA segment(s) for expression in a prokaryotic system may be performed by techniques generally known to those of skill in the art.

It is proposed that transformation of host cells with DNA segments encoding DsbC or DsbG and the protein of interest will provide a convenient means for obtaining high levels of active secreted polypeptide. However, separate expression followed by reconstitution or reactivation of the protein once secreted is also certainly within the scope of the invention. For example, the inventors contemplate that the extracellular addition of thiol reagents such as glutathione will be useful in enhancing the recovery of certain proteins in large quantity using the methods described herein. Both cDNA and genomic sequences are suitable for expression, as the host cell will, of course, process the genomic transcripts to yield functional mRNA for translation into protein.

For expression in this manner, one would position the coding sequences adjacent to and under the control of the promoter. It is understood in the art that to bring a coding sequence under the control of such a promoter, one positions the 5' end of the transcription initiation site of the transcriptional reading frame of the protein between about 1 and about 50 nucleotides "downstream" of (i.e., 3' of) the chosen promoter.

In accordance with the general guidelines described above, a preferred method for expressing human tPA DNA has been found to be the transformation of E. coli SF103 cells with the expression vectors termed ptPA177, pSE420dsbCm and pTrcdsbG. The ptPA177 expression vector is constructed from pACYC184, and contains the OmpA leader-tPA gene fusion.

Likewise, a preferred expression system for preparing bovine PTI is E. coli SF103 transformed with an expression system comprising pACYCBPTI and pSE420dsbC. The pACYCBPTI expression vector is constructed from pACYC184, and contains the OmpA leader-BPTI gene fusion. pSE420dsbC is constructed from pSE420 and contains dsbC.

Preferred expression systems for the production of recombinant proteins may be contained either on a single plasmid vector encoding DsbC or DsbG and the protein of interest.

It is contemplated that the recombinant polypeptides of the invention may be "overexpressed", i.e., expressed in increased levels relative to its natural expression in eukaryotic cells, or even relative to the expression of other proteins in the recombinant prokaryotic host cells. Such overexpression may be assessed by a variety of methods, including radio-labeling and/or protein purification. However, simple and direct methods are preferred, for example, those involving SDS/PAGE and protein staining or Western blotting, followed by quantitative analyses, such as densitometric scanning of the resultant gel or blot. A specific increase in the level of the recombinant protein or peptide in comparison to the level in native cells is indicative of overexpression, as is a relative abundance of the specific protein in relation to the other proteins produced by the host cell and, e.g., visible on a gel.

As used herein, the term "engineered" or "recombinant" cell is intended to refer to a cell into which a recombinant gene, such as a gene encoding the foldase along with a gene encoding a disulfide bond-containing polypeptide of interest (e.g., tPA) have been introduced. Therefore, engineered cells are distinguishable from naturally occurring cells which do not contain a recombinantly introduced gene. Engineered cells are thus cells having a gene or genes introduced through the hand of man. Recombinantly introduced genes will either be in the form of a cDNA gene (i.e., they will not contain introns), a copy of a genomic gene, or will include genes positioned adjacent to a promoter not naturally associated with the particular introduced gene.

Generally speaking, it may be more convenient to employ as the recombinant gene a cDNA version of the gene. It is believed that the use of a cDNA version will provide advantages in that the size of the gene will generally be much smaller and more readily employed to transfect the targeted cell than will a genomic gene, which will typically be up to an order of magnitude larger than the cDNA gene. However, the inventors do not exclude the possibility of employing a genomic version of a particular gene where desired. Where the introduction of a recombinant version of one or more of the foregoing genes is required, it will be important to introduce the gene such that it is under the control of a promoter that effectively directs the expression of the gene in the bacterial cell.

2.10 Purification of Recombinant Polypeptides

Further aspects of the present invention concern the purification, and in particular embodiments, the substantial purification, of a disulfide bond-containing polypeptide, and in particular a purified tPA or purified PTI protein composition. The term "purified tPA" as used herein, is intended to refer to a tPA composition, isolatable from recombinant bacterial host cells, wherein the tPA is purified to any degree relative to its naturally-obtainable state, i.e., in this case, relative to its purity within a cell extract. A purified tPA composition therefore also refers to a tPA polypeptide, free from the environment in which it may naturally occur or from the recombinant host cell in which it was produced. Likewise, the term "purified PTI" as used herein, is intended to refer to a PTI composition, isolatable from recombinant bacterial host cells, wherein the PTI is purified to any degree relative to its naturally-obtainable state, i.e., in this case, relative to its purity within a cell extract. A purified PTI composition therefore also refers to a PTI polypeptide, free from the environment in which it may naturally occur or from the recombinant host cell in which it was produced.

Generally, "purified" will refer to a tPA or PTI polypeptide composition which has been subjected to fractionation to remove various recombinant host cell components, and which composition substantially retains its tPA or PTI activity. Where the term "substantially purified" is used, this will refer to a composition in which the protein of interest forms the major component of the composition, such as constituting about 25%, about 50%, or even about 75% or greater of the soluble proteins isolated from the periplasm of the recombinant host cells described herein. "Purified" also refers to a protein or polypeptide composition which has been subjected to fractionation to remove various non-peptide components such as other cell components. Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques.

Various methods for quantifying the degree of purification of such peptides will be known to those of skill in the art in light of the present disclosure. These include, for example, determining the specific activity of an active fraction, or assessing the number of polypeptides within a fraction by SDS/PAGE analysis. For example, a preferred method for assessing the purity of a tPA composition is to calculate the specific activity of the fraction containing the tPA composition, to compare it to the specific activity of the initial soluble protein extract, and to thus calculate the degree of purity, herein assessed by a "-fold purification number".

As is generally known in the art, to determine the specific activity, one would calculate the number of units of activity per milligram of total protein. In the purification procedure, the specific activity of the starting material, i.e., of the soluble periplasmic extract, would represent the specific activity of the protein of interest in its un-purified state. At each step in the purification and concentration of the protein of interest, one would generally expect the specific activity of the particular enzyme to increase above this value, as it is purified relative to its un-purified state. In preferred embodiments, it is contemplated that one would assess the degree of purity of a given periplasmic fraction comprising recombinant tPA or PTI by comparing its specific activity to the specific activity of the starting material, and representing this as x-fold purification. The use of "fold purification" is advantageous as the purity of an inhibitory fraction can thus be compared to another despite any differences which may exist in the actual units of activity or specific activity.

As mentioned above, although preferred for use in certain embodiments, there is no general requirement that the recombinant polypeptides always be provided in their most purified state. Indeed, it is contemplated that less substantially purified polypeptides, which are nonetheless enriched in activity relative to the natural state, will have utility in certain embodiments. Partially purified disulfide bond-containing recombinant polypeptide fractions for use in such embodiments may be obtained by subjecting a recombinant host cell periplasmic fraction to one or a combination of the purification steps commonly used for their purification from soluble fractions as described above.

2.11 TPA and TPA Variants

In addition to native tPA, the inventors contemplate the production of tPA variants and derivatives using the disclosed method. Preferred tPA variants contemplated to be useful in the practice of the present invention include:

(1) tPA variants which have an extra glycosylation site at amino acid positions 103–105, the native glycosylation site removed at position 117, and at least one amino acid substituted in the 296–299 amino acid region of native human tPA. A specific molecule within this group is T103N, N117Q, KHRR (9296-299)AAAA tPA (TNK tPA), where the amino acids replaced are indicated to the left and the amino acids substituted for them to the right of the amino acid position(s) shown. These molecules, which have an extended half-life and improved fibrin specificity as compared to wild-type human tPA, and show substantial resistance to the fast acting plasminogen activator inhibitor (PAI-1), are specifically disclosed, for example, in Intl. Pat. Appl. Publ. No. WO/93/24635.

(2) N-terminally truncated tPA variants, and specifically the plasminogen activator K2P (BM 06.002) described, for example, in Eur. Pat. Appl. No. EP 0382174. The latter variants consists of the kringle 2 (K2) and protease (P) domains of human tPA, and due to its expression in E. coli is present in an unglycosylated form. K2P has been described to have a reduced clearance and a longer plasma half-life. Further tPA variants of this kind are described in the following patent publications: Eur. Pat. Appl. No. EP 196920; Eur. Pat. Appl. No. EP 207589; Aust. Pat. Appl. No. AU 61804/86; Eur. Pat. Appl. No. EP 231624; Eur. Pat. Appl. No. EP 289508; Eur. Pat. Appl. No. EP 234051; Eur. Pat. Appl. No. EP 263172; Eur. Pat. Appl. No. EP 24208; Eur. Pat. Appl. No. EP 292009; Eur. Pat. Appl. No. EP 297066; Eur. Pat. Appl. No. EP 302456; Eur. Pat. Appl. No. EP 379890.

(3) Vampire bat tPAs (BatPAs), as disclosed in Eur. Pat. Appl. No. EP 352119; and (4) A tPA variant having cysteine at position 84 of native tPA replaced by serine (C84A tPA), described, e.g., in Suzuki et al. (1993).

3. BRIEF DESCRIPTION OF THE DRAWINGS

The drawings form part of the present specification and are included to further demonstrate certain aspects of the present invention. The invention may be better understood by reference to one or more of these drawings in combination with the detailed description of specific embodiments presented herein.

FIG. 1A (Scanned image). Fibrin plate analysis of htPA activity. Equal amounts of soluble E. coli protein from each culture were spotted on the fibrin plate.

A: pBAD-stII-tPA alone

B: pBAD-stII-tPA+pLppLacOmpArPDI

C: pBAD-stII-tPA+pSE380dsbA;

D: pBAD-stII-tPA+pSE420dsbC,

E: pBAD-stII-tPA+pSE380dsbAC.

Figure 1B:
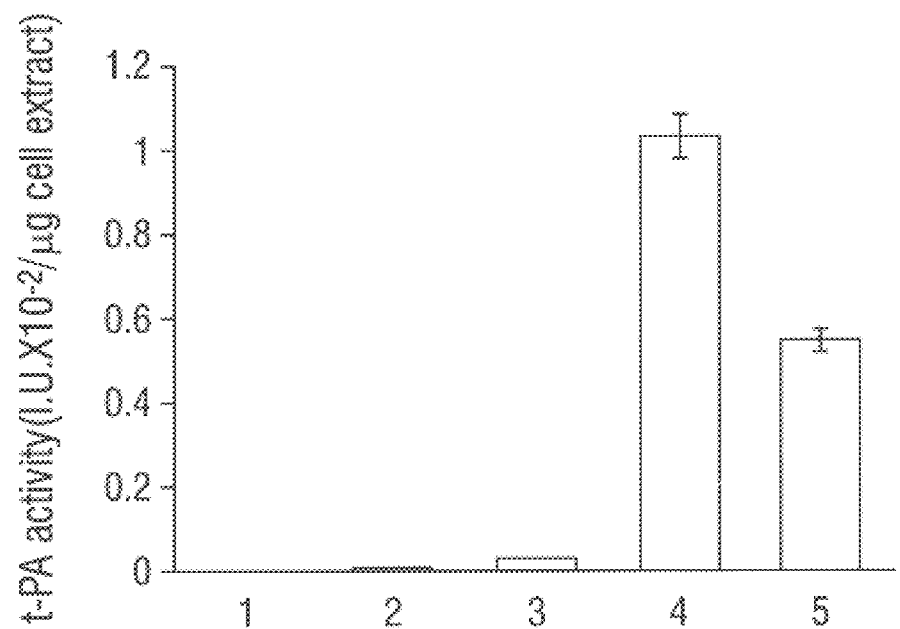

FIG. 1B. Specific rate of plasminogen activation, in cells expressing rPDI, DsbA or DsbC. The tPA activity in soluble fractions from cells harvested three hr after induction was measured by the indirect chromogenic assay. Sample 1, pBAD-stII-tPA alone; 2, pBAD-stII-tPA+ pLppLacOmpArPDI; 3, pBAD-stII-tPA+pSE380dsbA; 4, pBAD-stII-tPA+pSE420dsbC; and 5, pBAD-stII-tPA+ pSE380dsbAC.

Figure 1C:
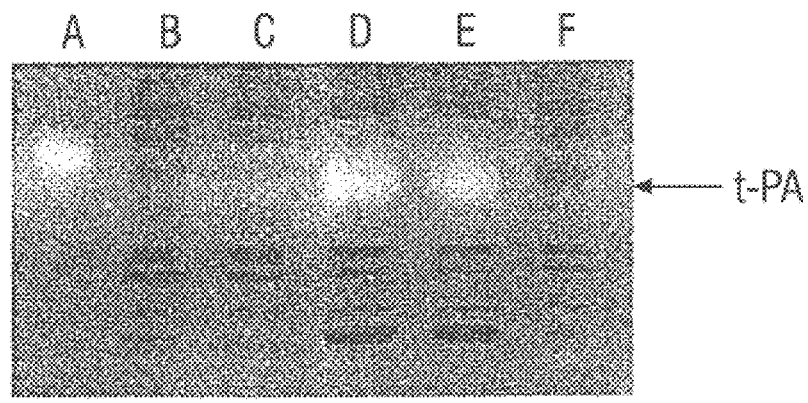

FIG. 1C (Scanned image). Zymography of $E.$ $coli$ soluble fractions. DsbC is evident as an intense Coomassie-stained band. Lane A, Single-chain tPA standard; lane B, pBAD-stII-tPA; lane C, pBAD-stII-tPA/pLppLacOmpArPDI; lane D, pBAD-stII-tPA/pSE380dsbA; lane E, pBAD-stII-tPA/ pSE420dsbC; and lane F, pBAD-stII-tPA/pSE380dsbAC.

Figure 1D:
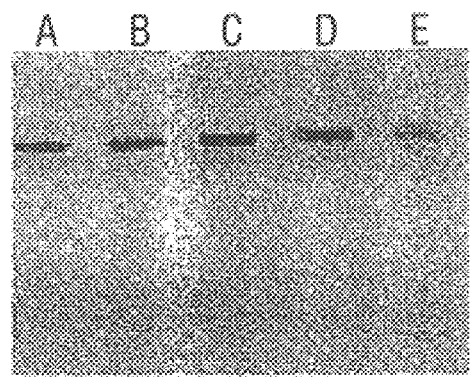

FIG. 1D (Scanned image). Western blot of tPA expression in different strains. Lane A, pBAD-stII-tPA; lane B, pBAD-stII-tPA+pSE380dsbA; lane C, pBAD-stII-tPA+ pSE420dsbC; lane D, pBAD-stII-tPA+pSE380dsbAC; and lane E, pBAD-stII-tPA+pLppLacOmpArPDI.

Figure 2:
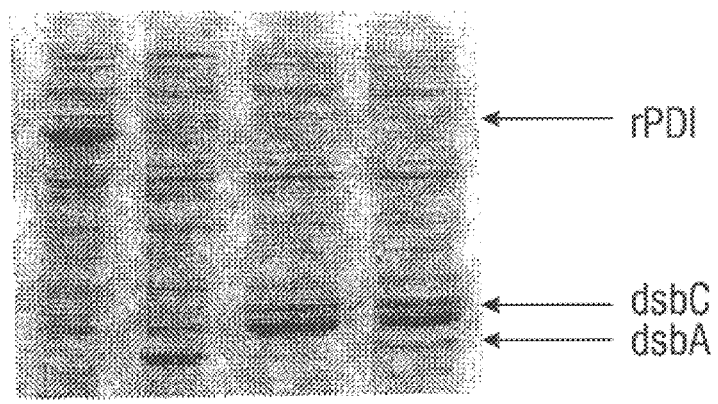

FIG. 2 (Scanned image). SDS-PAGE of total cell extracts from cultures coexpressing tPA and DsbA, DsbC and DsbA+ DsbC accumulation in cells co-expressing tPA. Cells were harvested 3 hr after induction, lysed and equal amounts of total protein were loaded on a 12% polyacrylamide SDS-PAGE gels were performed as described in Section 5. Lane A, pBAD-stII-tPA+pLppLacOmpArPDI; lane B, pBAD-stII-tPA+pSE380dsbA; lane C, pBAD-stII-tPA+ pSE420dsbC; and lane D, pBAD-stII-tPA+pSE380dsbAC.

Figure 3:
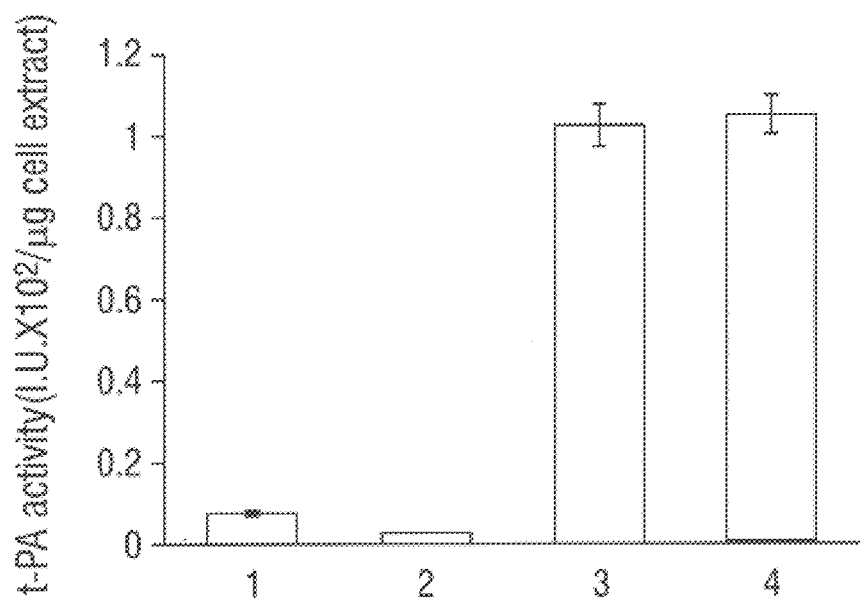

FIG. 3. The effects of glutathione on the specific rate of plasminogen activation by tPA. Cells were grown in LB media as described herein. When the cultures reached on $O.D._{600}$ of 0.8 the expression of DsbC was induced by adding 2 mM IPTG. At the same time reduced and/or oxidized glutathione were added as follows: #1: 2 mM GSH; #2: 0.5 mM GSSG; #3: 2.0 mM GSH +0.5 mM GSSG; #4: no addition. Synthesis of tPA was induced 30 min later and the cells were harvested after 3 hr. Mean and standard errors are given for 3 separate cultures with 3 replicates per assay (9 total determinations).

Figure 4:
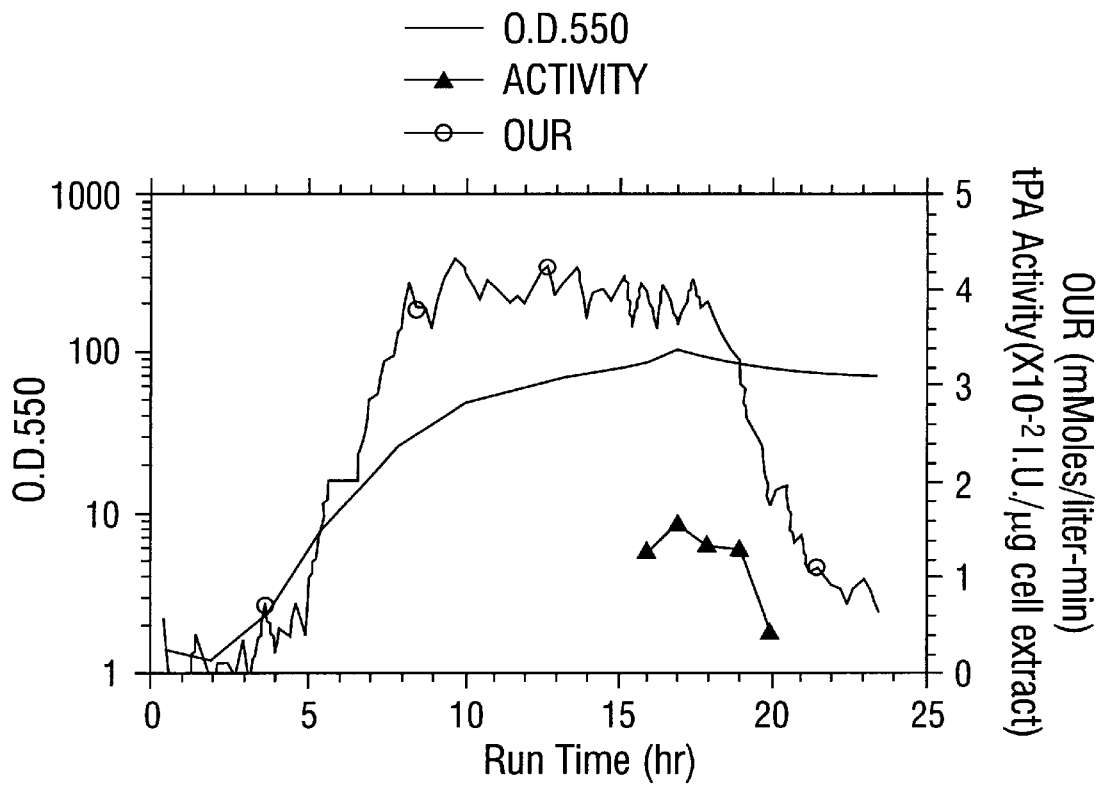

FIG. 4. $O.D._{550}$ and OUR (oxygen uptake rate) data for fermentation. Fermentation was performed as described in Section 5. 0.05 mM IPTG was added at 15 hr, and 0.1% arabinose at 15.5 hr. Activity from samples taken 0.5 hr, 1.5 hr, 2.5 hr, 3.5 hr, 4.5 hr, and 5.5 hr after addition of arabinose was assayed by indirect chromogenic assay.

Figure 5:
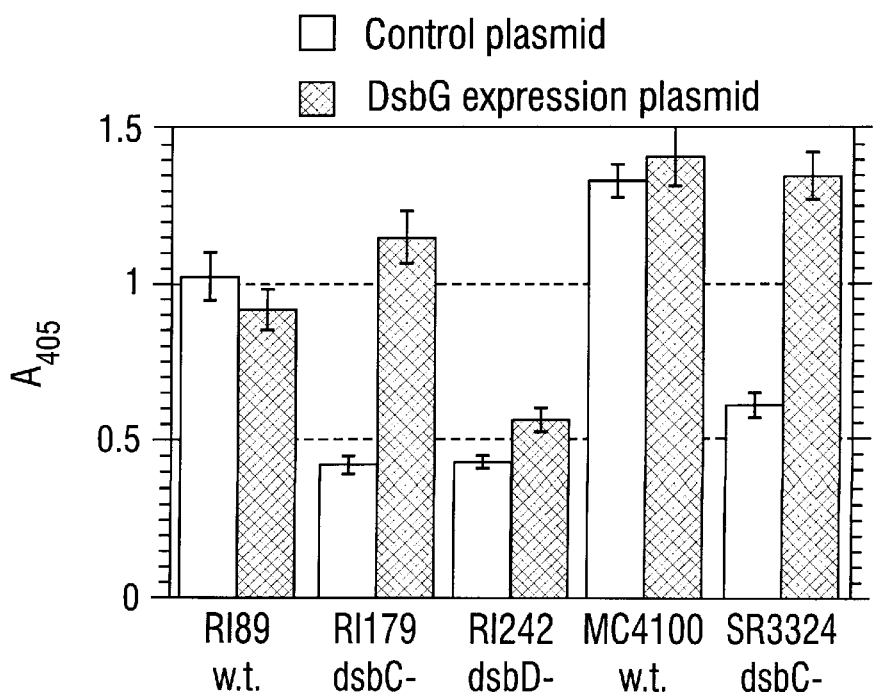

FIG. 5. BPTI expression as determined by ELISA. Absorbance at 405 nm is relative to the yield of correctly folded BPTI.

4. DESCRIPTION OF ILLUSTRATIVE EMBODIMENTS

4.1 Definitions

As used herein, "dsbC" refers to a gene encoding the bacterial periplasmic protein known in the literature as DsbC. As used herein, "dsbG" refers to a gene encoding the bacterial periplasmic protein known in the literature as DsbG. These genes may be isolated from any bacterial source, with one example being the dsbC and dsbG genes from $E.$ $coli$ as described by Missiakas et al. (1994). The dsbC or dsbG gene as used herein do not include PDI or any other eukaryotic protein that functions as a protein disulfide isomerase, including those disclosed in U.S. Pat. Nos. 5,270, 181 and 5,292,646; Jap. Pat. Appl. No. JP 60-38771; Intl. Pat. Appl. Publ. No. WO 93/25676; Eur. Pat. Appl. No. EP 293,793; Intl. Pat. Appl. Publ. No. WO 94/08012; and Eur. Pat. Appl. No. EP 509,841, all supra.

DsbC differs in many respects from PDI. For example, DsbC retains its isomerase activity in the absence of redox buffer, whereas PDI requires a redox buffer for its isomerase activity. Further, DsbC has a molecular weight by sequence analysis of 25 kDa, and contains four cysteine residues. In contrast, PDI has a molecular weight by sequence analysis of 57 kDa and contains six cysteine residues.

As used herein, "signal sequence" or "signal polypeptide" refers to a peptide that can be used to secrete the heterologous polypeptide into the periplasm or medium of the cultured bacteria or to secrete the DsbC or DsbG proteins into the periplasm. The signals for the heterologous polypeptide may be homologous to the bacteria, or they may be heterologous, including signals native to the polypeptide being produced in the bacteria. For dsbC, the signal sequence is typically that which is endogenous to the bacterial cells, although it need not be as long as it is effective for its purpose.

An "over-expressed" gene product is one that is expressed at levels greater than normal endogenous expression for that gene product. It can be accomplished, e.g., by introducing a recombinant construction that directs expression of a gene product in a host cell, or by altering basal levels of expression of an endogenous gene product, e.g., by inducing its transcription.

The promoters of this invention are "inducible" promoters, i.e., promoters which direct transcription at an increased or decreased rate upon binding of a transcription factor.

"Transcription factors" as used herein include any factors that can bind to a regulatory or control region of a promoter and thereby effect transcription. The synthesis or the promoter binding ability of a transcription factor within the host cell can be controlled by exposing the host to an "inducer" or removing an inducer from the host cell medium. Accordingly, to regulate expression of an inducible promoter, an inducer is added or removed from the growth medium of the host cell.

As used herein, the phrase "induce expression" means to increase the amount of transcription from specific genes by exposure of the cells containing such genes to an effector or inducer.

An "inducer" is a chemical or physical agent which, when given to a population of cells, will increase the amount of transcription from specific genes. These are usually small molecules whose effects are specific to particular operons or groups of genes, and can include sugars, phosphate, alcohol, metal ions, hormones, heat, cold, and the like. For example, isopropylthio-β-galactoside (IPTG) and lactose are inducers of the tacII promoter, and L-arabinose is a suitable inducer of the arabinose promoter. The pho gene promoter, such as phoA and pho5, is inducible by low phosphate concentrations in the medium.

As used herein, "polypeptide" or "polypeptide of interest" refers generally to peptides and proteins having more than about ten amino acids. Preferably, the polypeptides are "exogenous," meaning that they are "heterologous," i.e., foreign to the host cell being utilized, such as a human protein produced by a CHO cell, or a yeast polypeptide produced by a mammalian cell, or a human polypeptide produced from a human cell line that is not the native source of the polypeptide.

Examples of mammalian polypeptides include molecules such as, e.g., renin, a growth hormone, including human growth hormone; bovine growth hormone; growth hormone releasing factor; parathyroid hormone; thyroid stimulating hormone; lipoproteins; a1-antitrypsin; insulin A-chain; insulin β-chain; proinsulin; thrombopoietin; follicle stimulating hormone; calcitonin; luteinizing hormone; glucagon; clotting factors such as factor VIIIC, factor IX, tissue factor, and von Willebrands factor; anti-clotting factors such as Protein C; atrial naturietic factor; lung surfactant; a plasminogen activator, such as human tPA or urokinase; mammalian trypsin inhibitor, brain-derived neurotrophic growth factor (BDNF), kallikreins, CTNF, gp120, anti-HER-2, DNase, IGF-I, IGF-II, brain IGF-I, growth hormone, growth hormone releasing factor, human chorionic gonadotropin, mammalian pancreatic trypsin inhibitor, antibody fragments, insulin, protease inhibitors, therapeutic enzymes, lymphokines, cytokines, growth factors, neurotrophic factors, insulin chains or pro-insulin, immunotoxins, bombesin, thrombin, tumor necrosis factor-α and -β, enkephalinase, a serum albumin such as human serum albumin, mullerian-inhibiting substance, relaxin A-chain, relaxin B-chain, prorelaxin, mouse gonadotropin-associated peptide, a microbial protein, such as β-lactamase, DNase, inhibin, activin, vascular endothelial growth factor (VEGF), receptors for hormones or growth factors, integrin, protein A or D, rheumatoid factors, neurotrophic factors such as neurotrophin-3, -4, -5, or -6 (NT-3, NT-4, NT-5, or NT-6), or a nerve growth factor such as NGF-β, cardiotrophins (cardiac hypertrophy factor) such as cardiotrophin-1 (CT-1), platelet-derived growth factor (PDGF), fibroblast growth factor such as αFGF and βFGF, epidermal growth factor (EGF), transforming growth factor (TGF) such as TGF-α and TGF-β, including TGF-β1, TGF-β2, TGF-β3, TGF-β4, or TGF-β5, insulin-like growth factor-I and -II (IGF-I and IGF-II), des(1-3)-IGF-I (brain IGF-I), insulin-like growth factor binding proteins, CD proteins such as CD-3, CD-4, CD-8, and CD-19, erythropoietin, osteoinductive factors, immunotoxins, bone morphogenetic proteins (BMPs), interferons such as interferon-α, -β, and -γ, colony stimulating factors (CSFs), e.g., M-CSF, GM-CSF, and G-CSF, interleukins (Ils) such as IL-1 to IL-10, anti-HER-2 antibody, superoxide dismutase, T-cell receptors, surface membrane proteins, decay accelerating factor, viral antigens such as a portion of the AIDS envelope, transport proteins, homing receptors, addressins, regulatory proteins, antibodies, antigens such as gp120(IIIb), NGF, NT-3, NT-4, NT-5, and NT-6, or derivatives or active fragments of any of the peptides listed herein.

The polypeptides may be native or mutated polypeptides, and preferred sources for such mammalian polypeptides include human, bovine, equine, porcine, lupine, and rodent sources, with human proteins being particularly preferred.

The expression "control sequences" refers to DNA sequences necessary for the expression of an operably linked coding sequence in a particular host organism. The control sequences that are suitable for bacteria include the alkaline phosphatase promoter, optionally an operator sequence, and a ribosome-binding site.

Nucleic acid is "operably" or "operatively" linked when it is placed into a functional relationship with another nucleic acid sequence. For example, DNA for a presequence or secretory leader is operably/operatively linked to DNA for a polypeptide if it is expressed as a preprotein that participates in the secretion of the polypeptide; a promoter or enhancer is operably/operatively linked to a coding sequence if it affects the transcription of the sequence; or a ribosome binding site is operably linked to a coding sequence if it is positioned so as to facilitate translation. Generally, "operably linked" or "operatively linked" means that the DNA sequences being linked are contiguous and, in the case of a secretory leader, contiguous and in reading phase. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

4.2 DsbC and DsbG

DsbC is a soluble periplasmic oxidoreductase which is thought to act in parallel with DsbA (Missiakas et al., 1994; Bardwell, 1994a; 1994b). Unlike DsbA which exhibits low disulfide isomerase activity in vitro, DsbC has been shown to be an efficient catalyst of disulfide bond isomerization (Zapun et al., 1995).

DsbG is a soluble periplasmic oxidoreductase which has properties similar to DsbC. Unlike DsbA which exhibits low disulfide isomerase activity in vitro, the inventors have shown that DsbG is an efficient catalyst of disulfide bond isomerization.

4.3 Methods of Nucleic Acid Delivery and DNA Transformation

In yet another embodiment, the present invention provides recombinant host cells transformed with polynucleotides which encode DsbC, and particular disulfide bond-containing polypeptides of interest, as well as transgenic cells derived from those transformed or transfected cells. Preferably, a recombinant host cell of the present invention is transformed with a polynucleotide comprising a sequence encoding DsbC and a polynucleotide comprising a sequence encoding either tPA or PTI. Means of transforming cells with exogenous polynucleotide such as DNA molecules are well known in the art and include techniques such as calcium-phosphate- or DEAE-dextran-mediated transfection, protoplast fusion, electroporation, liposome mediated transfection, direct microinjection and adenovirus infection (Sambrook et al., 1989).

The application of brief, high-voltage electric pulses to a cell culture leads to the formation of nanometer-sized pores in the cell membrane. DNA is taken directly into the cytoplasm either through these pores or as a consequence of the redistribution of membrane components that accompanies closure of the pores. Electroporation can be extremely efficient and can be used both for transient expression of cloned genes and for establishment of cell lines that carry integrated copies of the gene of interest. Electroporation, in contrast to calcium chloride-mediated transformation, frequently gives rise to high numbers of target cells being transformed with the foreign DNA.

Liposome transfection involves encapsulation of DNA and RNA within liposomes, followed by fusion of the liposomes with the cell membrane. The mechanism of how DNA is delivered into the cell is unclear but transfection efficiencies can be as high as 90%.

4.4 Liposomes and Nanocapsules

In certain embodiments, the inventors contemplate the use of liposomes and/or nanocapsules for the introduction of particular peptides or nucleic acid segments into host cells. Such formulations may be preferred for the introduction of nucleic acids, peptides, and/or antibodies derived therefrom. The formation and use of liposomes is generally known to those of skill in the art (see, e.g., Couvreur et al., 1977 which describes the use of liposomes and nanocapsules in the targeted antibiotic therapy of intracellular bacterial infections and diseases). Recently, liposomes were developed with improved serum stability and circulation half-times (Gabizon and Papahadjopoulos, 1988).

Nanocapsules can generally entrap compounds in a stable and reproducible way (Henry-Michelland et al., 1987). To avoid side effects due to intracellular polymeric overloading, such ultrafine particles (sized around 0.1 $\mu$m) should be designed using polymers able to be degraded in vivo. Biodegradable polyalkyl-cyanoacrylate nanoparticles that meet these requirements are contemplated for use in the present invention, and such particles may be are easily made, as described (Couvreur et al., 1977; 1988).

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 pm. Sonication of MLVs results in the formation of small unilamellar vesicles (SUVs) with diameters in the range of 200 to 500 Å, containing an aqueous solution in the core.

In addition to the teachings of Couvreur et al. (1988), the following information may be utilized in generating liposomal formulations. Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

Liposomes interact with cells via four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. It often is difficult to determine which mechanism is operative and more than one may operate at the same time.

4.5 Recombinant Expression of Heterologous Proteins in Bacteria

The present inventors contemplate cloning the recombinant polypeptides identified herein, and in particular recombinant tPA and PTI polypeptides. A technique often employed by those skilled in the art of protein production today is to obtain a so-called "recombinant" version of the protein, to express it in a recombinant cell and to obtain the protein from such cells. These techniques are based upon the "cloning" of a DNA molecule encoding the protein from a DNA library, i.e., on obtaining a specific DNA molecule distinct from other portions of DNA. This can be achieved by, for example, cloning a cDNA molecule, or cloning a genomic-like DNA molecule. Techniques such as these would also, of course, be appropriate for the production of a disulfide bond-containing polypeptide in accordance with the present invention.

The first step in such cloning procedures is the screening of an appropriate DNA library, such as, in the present case, a rat, human, bovine, or other mammalian-derived library. The screening procedure may be an expression screening protocol employing antibodies directed against the protein, or activity assays. Alternatively, screening may be based on the hybridization of oligonucleotide probes, designed from a consideration of portions of the amino acid sequence of the protein, or from the DNA sequences of genes encoding related proteins. The operation of such screening protocols are well known to those of skill in the art and are described in detail in the scientific literature, for example, in Sambrook et al. (1989) specifically incorporated herein by reference. Moreover, as the present invention encompasses the cloning of genomic segments as well as cDNA molecules, it is contemplated that other suitable methods known to those in the art, such as, e.g., those described by Spoerel et al. (1987), may also be used in connection with cloning a disulfide bond-containing polypeptide, or alternatively an eukaryotic foldase to direct the folding and isomerization of disulfide bonds contained within such polypeptides of interest.

After identifying appropriate DNA molecules, they may be inserted into any one of the many vectors currently known in the art and transferred to a prokaryotic or eukaryotic host cell where it will direct the expression and production of the so-called recombinant version of the protein. This is also, of course, routinely practiced in the art and described in various publications, such as, e.g., Sambrook et al. (1989). Such DNA segments may be contained on a single plasmid vector, or alternatively, the foldase may be encoded by nucleic acid sequences on one vector and the disulfide bond-containing polypeptide of interest may be present on a second plasmid vector which is compatible for co-residence in a single host cell with the first plasmid vector comprising the foldase sequence. The selection of plasmid vectors is well-known to those of skill in the art, and such a selection may be based on the incompatibility grouping of such vectors (IncP, IncQ, etc.). Virtually any such plasmid vectors may be used in the practice of the invention so long as they are replicable in the appropriate prokaryotic host cell employed. In one embodiment, preferred replicons include pACYC184 and pTI103.

It will be understood that recombinant disulfide bond-containing polypeptides may differ from naturally-produced polypeptides in certain ways. In particular, the degree of post-translational modifications, such as, for example, glycosylation and phosphorylation may be different between the recombinant and natural forms.

Recombinant clones expressing nucleic acid segments which encode eukaryotic disulfide-bond containing polypeptides may be used to prepare purified recombinant polypeptides, purified polypeptide-derived antigens as well as mutant or variant recombinant protein species in significant quantities. In particular, the invention provides for the production of recombinant tPA (rtPA) or recombinant PTI (rPTI) in substantial quantities from bacterial host cells.

Additionally, by application of techniques such as DNA mutagenesis, the present invention allows the ready preparation of so-called "second generation" molecules having modified or simplified protein structures. Second generation proteins will typically share one or more properties in common with the full-length polypeptides, such as a particular antigenic/immunogenic epitopic core sequences, or particular catalytic sites, active sites, or ligand binding domains, etc. Epitopic sequences can be provided on relatively short molecules prepared from knowledge of the peptide, or encoding DNA sequence information. Such variant molecules may not only be derived from selected immunogenic/antigenic regions of the protein structure, but may additionally, or alternatively, include one or more functionally equivalent amino acids selected on the basis of similarities or even differences with respect to the natural sequence. This is particularly desirable in the preparation of recombinant polypeptides having enhanced or superior stability, activity, binding, or affinity for substrates and the like.

The general process of recombinant expression of proteins in bacterial hosts, and particularly Gram-negative hosts, is well-known to those of skill in the art. It is generally preferred for the methods described herein that the DNA sequence encoding the particular eukaryotic protein of interest to be secreted be operatively linked to a DNA sequence which encodes a signal peptide sufficient for the translocation of the recombinant polypeptide to the periplasmic space of the bacterial host cell. As it is well-known, operative links between such DNA sequences mean that a translational fusion exists between the heterologous protein and the signal peptide. As a rule, such signal peptides form the N-terminal portion of the secreted heterologous protein. Signal sequences which promote protein translocation to the periplasmic space of Gram-negative bacterial are well-known, as exemplified by those described herein. The *E. coli* OmpA, Lpp, LamB, MalE, PelB, and StII leader peptide sequences have been successfully used in many applications as signal sequences to promote protein secretion in bacterial cells such as those used herein, and are all contemplated to be useful in the practice of the invention.

4.6 Promoters, Enhancers, and Signal Sequence Elements

The promoters and enhancers that control the transcription of protein-encoding genes are composed of multiple genetic elements. The cellular machinery is able to gather and integrate the regulatory information conveyed by each element, allowing different genes to evolve distinct, often complex patterns of transcriptional regulation.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator proteins. At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV 40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between elements is flexible, so that promoter function is preserved when elements are inverted or moved relative to one another. In the tk promoter, the spacing between elements can be increased to 50 bp apart before activity begins to decline. Depending on the promoter, it appears that individual elements can function either cooperatively or independently to activate transcription.

Enhancers were originally detected as genetic elements that increased transcription from a promoter located at a distant position on the same molecule of DNA. This ability to act over a large distance had little precedent in classic studies of prokaryotic transcriptional regulation.

Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Aside from this operational distinction, enhancers and promoters are very similar entities. They have the same general function of activating transcription in the cell. They are often overlapping and contiguous, often seeming to have a very similar modular organization. Taken together, these considerations suggest that enhancers and promoters are homologous entities and that the transcriptional activator proteins bound to these sequences may interact with the cellular transcriptional machinery in fundamentally the same way.

Particularly preferred promoters include the lac-lpp promoter which is well-known in the art. Other promoters contemplated to be useful in the practice of the invention include the ara, tet, tac, trc, trp, phoA, $P_{BAD}$, $\lambda_{PL}$, lpp, and the T7 promoters.

4.7 Site-Specific Mutagenesis

Site-specific mutagenesis is a technique useful in the preparation of individual peptides, or biologically functional equivalent proteins or peptides, through specific mutagenesis of the underlying DNA. The technique, well-known to those of skill in the art, further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 14 to about 25 nucleotides in length is preferred, with about to about 10 residues on both sides of the junction of the sequence being altered.

In general, the technique of site-specific mutagenesis is well known in the art, as exemplified by various publications. As will be appreciated, the technique typically employs a phage vector which exists in both a single stranded and double stranded form. Typical vectors useful in site-directed mutagenesis include vectors such as the M13 phage. These phage are readily commercially-available and their use is generally well-known to those skilled in the art.

Double-stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart of two strands of a double-stranded vector which includes within its sequence a DNA sequence which encodes the desired peptide. An oligonucleotide primer bearing the desired mutated sequence is prepared, generally synthetically. This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected which include recombinant vectors bearing the mutated sequence arrangement.

The preparation of sequence variants of the selected peptide-encoding DNA segments using site-directed mutagenesis is provided as a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants. Specific details regarding these methods and protocols are found in the teachings of Maloy et al. (1994); Segal (1976); Prokop and Bajpai (1991); and Maniatis et al.(1982), each incorporated herein by reference, for that purpose.

The PCR™-based strand overlap extension (SOE) for site-directed mutagenesis is particularly preferred for site-directed mutagenesis of the nucleic acid compositions of the present invention. The techniques of PCR™ are well-known to those of skill in the art, as described hereinabove. The SOE procedure involves a two-step PCR™ protocol, in which a complementary pair of internal primers (B and C) are used to introduce the appropriate nucleotide changes into the wild-type sequence. In two separate reactions, flanking PCR™ primer A (restriction site incorporated into the oligo) and primer D (restriction site incorporated into the oligo) are used in conjunction with primers B and C, respectively to generate PCR™ products AB and CD. The PCR™ products are purified by agarose gel electrophoresis and the two overlapping PCR™ fragments AB and CD are combined with flanking primers A and D and used in a second PCR™ reaction. The amplified PCR™ product is agarose gel purified, digested with the appropriate enzymes, ligated into an expression vector, and transformed into *E. coli* JM101, XL1-Blue® (Stratagene, La Jolla, Calif.), JM105, TG1 (Carter et al., 1985), or other such suitable cells as deemed appropriate depending upon the particular application of the invention. Clones are isolated and the mutations are confirmed by sequencing of the isolated plasmids. Beginning with the native gene sequences, for example, the nucleic acid sequences encoding eukaryotic disulfide-bond-containing polypeptides such as PTI or tPA and the like, suitable clones and subclones may be made in the appropriate vectors from which site-specific mutagenesis may be performed.

4.8 Biological Functional Equivalents

Modification and changes may be made in the structure of the peptides of the present invention and DNA segments which encode them and still obtain a functional molecule that encodes a protein or peptide with desirable characteristics. The following is a discussion based upon changing the amino acids of a protein to create an equivalent, or even an improved, second-generation molecule. The amino acid changes may be achieved by changing the codons of the DNA sequence, according to the data in Table 1.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982, incorporate herein by reference). It is accepted that the relative hydropathic character of the amino acid contributes to the secondary structure of the resultant protein, which in turn defines the interaction of the protein with other molecules, for example, enzymes,

TABLE 1

| Amino Acids | | | Codons |
| --- | --- | --- | --- |
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU | substrates, receptors, DNA, antibodies, antigens, and the like. Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, ie. still obtain a biological functionally equivalent protein. In making such changes, the substitution of amino acids whose hydropathic indices are within ±2 is preferred, those which are within ±1 are particularly preferred, and those within ±0.5 are even more particularly preferred. It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

4.9 Modes for Carrying Out the Invention

In the process herein, expression of the dsbC or dsbG gene is induced just before (immediately prior to) heterologous gene expression. The heterologous polypeptide and the DsbC or DsbG protein are both secreted into the periplasm or the heterologous polypeptide is secreted into the culture medium of the bacteria into which nucleic acid encoding these polypeptides has been introduced. Preferably, the polypeptide is recovered from the periplasm of the bacteria.

The dsbC or dsbG gene may be from any bacterial source, but preferably E. coli, and is generally the native sequence. It is suitably separately placed from the nucleic acid encoding the heterologous polypeptide if nucleic acids are on the same vector, i.e., they are not linked. In addition, the nucleic acid encoding DsbC or DsbG and the nucleic acid encoding the heterologous polypeptide are under separate, different inducible promoters so that induction of expression can occur in the required sequential order. The nucleic acid encoding DsbC or DsbG and the nucleic acid encoding the heterologous polypeptide may be integrated into the host cell genome or contained on autonomously replicating plasmids.

If DsbC or DsbG is a native product of the host cell, and if the factors controlling expression of this native gene is understood, such factors can be manipulated to achieve over-expression of the dsbC or dsbG gene, e.g., by induction of transcription from the natural promoter using known inducer molecules, by mutation of the nucleic acids controlling or repressing expression of the gene product to produce a mutant strain that inductively over-expresses the gene product, by second site mutations which depress the synthesis or function of factors that normally repress the transcription of the gene product, and the like.

In one alternative, the bacteria comprises two separate vectors respectively containing the nucleic acid encoding the DsbC or DsbG protein and the nucleic acid encoding the heterologous polypeptide.

In another alternative, the nucleic acid encoding the DsbC or DsbG protein and the nucleic acid encoding the heterologous polypeptide are contained on the same vector but are under the control of separate inducible promoters and separate signal sequences.

In a third alternative, the nucleic acid encoding DsbC and DsbG and the nucleic acid encoding the heterologous polypeptide are contained on the same vector and are under the control of a single promoter.

The heterologous nucleic acid (e.g., cDNA or genomic DNA) is suitably inserted into a replicable vector for expression in the bacterium under the control of a suitable promoter for bacteria. Many vectors are available for this purpose, and selection of the appropriate vector will depend mainly on the size of the nucleic acid to be inserted into the vector and the particular host cell to be transformed with the vector. Each vector contains various components depending on its function (amplification of DNA or expression of DNA) and the particular host cell with which it is compatible. The vector components for bacterial transformation generally include, but are not limited to, one or more of the following: a signal sequence, an origin of replication, one or more marker genes, and an inducible promoter.

In general, plasmid vectors containing replicon and control sequences that are derived from species compatible with the host cell are used in connection with bacterial hosts. The vector ordinarily carries a replication site, as well as marking sequences that are capable of providing phenotypic selection in transformed cells. For example, E. coli is typically transformed using pBR322, a plasmid derived from an E. coli species (see, e.g., Bolivar et al., 1977). pBR322 contains genes for ampicillin and tetracycline resistance and thus provides easy means for identifying transformed cells. The pBR322 plasmid, or other microbial plasmid or phage, also generally contains, or is modified to contain, promoters that can be used by the microbial organism for expression of the selectable marker genes.

The DNA encoding the polypeptide of interest herein may be expressed not only directly, but also as a fusion with another polypeptide, preferably a signal sequence or other polypeptide having a specific cleavage site at the N-terminus of the mature polypeptide. In general, the signal sequence may be a component of the vector, or it may be a part of the polypeptide DNA that is inserted into the vector. The heterologous signal sequence selected should be one that is recognized and processed (i.e., cleaved by a signal peptidase) by the host cell. For bacterial host cells that do not recognize and process the native polypeptide signal sequence, the signal sequence is substituted by a bacterial signal sequence selected, for example, from the group consisting of the alkaline phosphatase, penicillinase, lpp, or heat-stable enterotoxin II leaders.

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria. The origin of replication from the plasmid pBR322 is suitable for most Gram-negative bacteria.

Expression and cloning vectors also generally contain a selection gene, also termed a selectable marker. This gene encodes a protein necessary for the survival or growth of transformed host cells grown in a selective culture medium.

Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli. One example of a selection scheme utilizes a drug to arrest growth of a host cell. Those cells that are successfully transformed with a heterologous gene produce a protein conferring drug resistance and thus survive the selection regimen.

The expression vector for producing a heterologous polypeptide also contains an inducible promoter that is recognized by the host bacterial organism and is operably linked to the nucleic acid encoding the polypeptide of interest. It also contains a separate inducible promoter operably linked to the nucleic acid encoding the DsbC protein. Inducible promoters suitable for use with bacterial hosts include the b-lactamase and lactose (lac) promoter systems (Chang et al., 1978; Goeddel et al., 1979), the arabinose (ara) promoter system (Guzman et al., 1992), alkaline phosphatase (phoA), a tryptophan (trp) promoter system (Goeddel, 1980; Eur. Pat. Appl. Publ. No. EP 36,776), $\lambda_{PL}$ promoter, and hybrid promoters such as the tac promoter. However, other known bacterial inducible promoters are suitable. Their nucleotide sequences have been published, thereby enabling a skilled worker operably to ligate them to DNA encoding the polypeptide of interest or to the dsbC gene (Siebenlist et al., 1980) using linkers or adaptors to supply any required restriction sites.

Promoters for use in bacterial systems also generally contain a Shine-Dalgarno (S.D.) sequence operably linked to the DNA encoding the polypeptide of interest. The promoter can be removed from the bacterial source DNA by restriction enzyme digestion and inserted into the vector containing the desired DNA. Construction of suitable vectors containing one or more of the above-listed components employs standard ligation techniques. Isolated plasmids or DNA fragments are cleaved, tailored, and re-ligated in the form desired to generate the plasmids required.

Suitable bacteria for this purpose include Archaebacteria and Eubacteria, especially Eubacteria, and most preferably Enterobacteriaceae. Examples of useful bacteria include Escherichia, Enterobacter, Azotobacter, Erwinia, Bacillus, Pseudomonas, Klebsiella, Proteus, Salmonella, Serratia, Shigella, Rhizobia, Vitreoscilla, and Paracoccus. Suitable *E. coli* hosts include *E. coli* SF110, *E. coli* 294 (ATCC 31446), *E. coli* B, and *E. coli* $\chi^{1776}$ *(ATCC 31537)*. These examples are illustrative rather than limiting. Mutant cells of any of the above-mentioned bacteria may also be employed. It is, of course, necessary to select the appropriate bacteria taking into consideration replicability of the replicon in the cells of a bacterium. For example, *E. coli*, Serratia, or Salmonella species can be suitably used as the host when well known plasmids such as pBR322, pBR325, pACYC177, or pKN410 are used to supply the replicon.

Host cells are transfected and preferably transformed with the above-described expression vectors and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ and electroporation. Successful transfection is generally recognized when any indication of the operation of this vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in section 1.82 of Sambrook et al., (1989), is generally used for bacterial cells that contain substantial cell-wall barriers. Another method for transformation employs polyethylene glycol/DMSO. Yet another method is the use of the technique termed electroporation.

Bacterial cells used to produce the polypeptide of interest for purposes of this invention are cultured in suitable media in which the promoters for the nucleic acid encoding the heterologous polypeptide and for the nucleic acid encoding DsbC can be artificially induced as described generally, e.g., in Sambrook et al. (1989). Examples of suitable media are given in U.S. Pat. Nos. 5,304,472 and 5,342,763(each specification incorporated herein by reference).

Any necessary supplements besides carbon, nitrogen, and inorganic phosphate sources may also be included at appropriate concentrations introduced alone or as a mixture with another supplement or medium such as a complex nitrogen source. The pH of the medium may be any pH from about 5–9, depending mainly on the host organism. Preferably, the medium contains no reduced glutathione, and the bacteria are not cultured so as to over-express nucleic acid encoding the heat-shock transcription factor, RpoH.

Gene expression may be measured in a sample directly, for example, by conventional northern blotting to quantitate the transcription of mRNA (Thomas, 1980). Various labels may be employed, most commonly radioisotopes, particularly $^{32}P$. However, other techniques may also be employed, such as using biotin-modified nucleotides for introduction into a polynucleotide. The biotin then serves as the site for binding to avidin or antibodies, which may be labeled with a wide variety of labels, such as radionuclides, fluorescers, enzymes, or the like.

Procedures for observing whether an expressed or over-expressed gene product is secreted are readily available to the skilled practitioner. Once the culture medium is separated from the host cells, for example, by centrifugation or filtration, the gene product can then be detected in the cell-free culture medium by taking advantage of known properties characteristic of the gene product. Such properties can include the distinct immunological, enzymatic, or physical properties of the gene product.

For example, if an over-expressed gene product has a unique enzyme activity, an assay for that activity can be performed on the culture medium used by the host cells. Moreover, when antibodies reactive against a given gene product are available, such antibodies can be used to detect the gene product in any known immunological assay (e.g., as in Harlowe and Lane, 1988).

The secreted gene product can also be detected using tests that distinguish polypeptides on the basis of characteristic physical properties such as molecular weight. To detect the physical properties of the gene product, all polypeptides newly synthesized by the host cell can be labeled, e.g., with a radioisotope. Common radioisotopes that can be used to label polypeptides synthesized within a host cell include tritium ($^{3}H$), carbon-14 ($^{14}C$), sulfur-35 ($^{35}S$), and the like. For example, the host cell can be grown in $^{35}S$-methionine or $^{35}S$-cysteine medium, and a significant amount of the $^{35}S$ label will be preferentially incorporated into any newly synthesized polypeptide, including the over-expressed heterologous polypeptide. The $^{35}$S-containing culture medium is then removed and the cells are washed and placed in fresh non-radioactive culture medium. After the cells are maintained in the fresh medium for a time and under conditions sufficient to allow secretion of the $^{35}$S-radiolabeled expressed heterologous polypeptide, the culture medium is collected and separated from the host cells. The molecular weight of the secreted, labeled polypeptide in the culture medium can then be determined by known procedures, e.g., polyacrylamide gel electrophoresis. Such procedures, and/or other procedures for detecting secreted gene products, are provided in Goeddel (1990), and Sambrook et al. (1989).

For secretion of an expressed or over-expressed gene product, the host cell is cultured under conditions sufficient for secretion of the gene product. Such conditions include, e.g., temperature, nutrient, and cell density conditions that permit secretion by the cell. Moreover, such conditions are those under which the cell can perform basic cellular functions of transcription, translation, and passage of proteins from one cellular compartment to another, as are known to those skilled in the art.

In practicing the process of this invention, the yield of total polypeptide is generally increased, while yield of insoluble polypeptide is not changed or is decreased, i.e., yield of soluble polypeptide is increased.

The polypeptide of interest is recovered from the periplasm or culture medium as a secreted soluble polypeptide. It is often preferred to purify the polypeptide of interest from recombinant cell proteins or polypeptides and from the DsbC protein to obtain preparations that are substantially homogeneous as to the polypeptide of interest. As a first step, the culture medium or lysate is centrifuged to remove particulate cell debris. The membrane and soluble protein fractions may then be separated if necessary. The polypeptide may then be purified from the soluble protein fraction and from the membrane fraction of the culture lysate, depending on whether the polypeptide is membrane associated or, more preferably, completely soluble in the periplasm or culture supernatant. The polypeptide thereafter may be further solubilized and/or refolded, if necessary, and purified from contaminant soluble proteins and polypeptides.

The types of phase-forming species to employ herein depend on many factors, including the type of polypeptide and the ingredients in the fermentation broth being treated. The species must be selected so that the polypeptide does not precipitate and one phase is more hydrophobic than the other phase so that the polypeptide will be located in the more hydrophobic phase and the biomass solids and nucleic acids will settle to the less hydrophobic phase.

The phase-forming species may be a combination of agents, including polymer combinations (polymer-polymer), polymer-salt combinations, solvent-salt, and polymer-solvent combinations. Suitable polymers are both highly hydrophilic polymers and less hydrophilic polymers, ie., any phase-forming polymers that are known in the art. Examples include polyethylene glycol or derivatives thereof, including various molecular weights of PEG such as PEG 4000, PEG 6000, and PEG 8000, derivatives of PEG described, for example, in Grunfeld et al. (1992), polyvinylpyrrolidone (PVP), in a preferable molecular weight range of about 36,000 to 360,000, starches such as dextran (e.g., dextran 70 and 500), dextrins, and maltodextrins (preferable molecular weight between about 600 and 5,000), sucrose, and Ficoll-400™ polymer (a copolymer of sucrose and epichlorohydrin). The preferred polymer herein is polyethylene glycol, polypropylene glycol, polyvinylpyrrolidone, or a polysaccharide such as a dextran. The most preferred polymer herein is PEG of different molecular weights or a PEG-polypropylene glycol combination or copolymer.

Examples of suitable organic solvents include ethylene glycol, glycerol, dimethyl sulfoxide, polyvinylalcohol, dimethylformamide, dioxane, and alcohols such as methanol, ethanol, and 2-propanol. Such solvents are such that, when added to aqueous solution, they increase the hydrophobicity of the solution.

The salts can be inorganic or organic and preferably do not act to precipitate the polypeptide. Salts containing transition elements are not preferred as they tend to precipitate the polypeptide. Anions are selected that have the potential for forming aqueous multiple-phase systems. Examples include ammonium sulfate, sodium dibasic phosphate, sodium sulfate, ammonium phosphate, potassium citrate, magnesium phosphate, sodium phosphate, calcium phosphate, potassium phosphate, potassium sulfate, magnesium sulfate, calcium sulfate, sodium citrate, manganese sulfate, manganese phosphate, etc. Preferred salts herein are sulfates, phosphates, or citrates and are alkali or alkaline earth metals. More preferred are sulfates and citrates, and most preferred are sulfates since there are fewer pH limitations with sulfates. The most preferred salts herein are sodium sulfate and sodium citrate.

The amounts of phase-forming species to add to the polypeptide of interest to obtain a satisfactory multiple-phase system are those known in the art. The amount of phase-forming species added to the polypeptide will depend on such factors as, for example, the amount of chaotropic agent and reducing agent, if any, already present in the fermentation broth, the nature of the cell culture media, the type of cells used in the fermentation, the type of polypeptide being treated, whether the polypeptide will be recovered from the lower or upper phase, and the type(s) of phase-forming species being added. The general concentration of polymer employed is about 5% (wt./wt.) up to the limit of solubility for the polymer and the concentration of salt employed is about 3% (wt./wt.) up to the limit of solubility for the salt, depending on the size of the phase-volume ratio needed. The phase-volume ratio must be sufficient to accommodate the biomass solids. The types and amounts of phase-forming species that are effective can be determined by phase diagrams and by evaluating the final result, i.e., the degree of purity and the yield of the polypeptide of interest. If the phase-forming species are a polymer-salt combination, preferably the concentration of salt added is about 4–15% (wt./wt.) and the concentration of polymer is 5–18% (wt./wt.) so that the desired polypeptide will be in an opposite phase from that in which the biomass solids and nucleic acids are present.

If the system desired is one where the polypeptide is distributed in the top phase and the biomass solids and nucleic acids are in the bottom phase, then there is a window of concentrations of phase-forming species. When higher amounts of chaotropic agent are added to maintain solubilization, the higher the amount of phase-forming species required. However, a high concentration of all these reagents will increase the density of the solution. A high density will cause the biomass solids to settle less readily. An overly high density will cause biomass solids to float on the surface. Hence, the concentrations of chaotropic agent and phase-forming species must be sufficiently high to maintain a fully solubilized polypeptide, but low enough to allow the biomass solids to sediment to the opposite (lower) phase.

If the polypeptide is to be recovered in the upper phase, typically the salt concentration will be about 4–7% (wt./wt.)

and the polymer concentration will be about 12–18% (wt./wt.), depending, e.g., on the type of salt, polymer, and polypeptide. If an organic solvent is added as a phase-forming species, such as ethanol, it is preferably added in a concentration of about 10 to 30% (vol./vol.) of the solution, depending, e.g., on the type of polypeptide and alcohol and if any other phase-forming species is present, preferably at a concentration of about 20% (vol./vol.).

The exact conditions for contacting the cell culture with the various reagents will depend on, e.g., the pH of the buffer, the types of phase-forming reagents, and the types and concentrations of polypeptide and chaotropic and reducing agents. The reaction temperature is generally about 20 to about 40° C., more preferably room temperature. The contacting step will generally be carried out for at least about 30 min., preferably about 30 min. to about 12 hr depending on whether side-reactions will occur, more preferably about 30 min. to about 8 hr, and most preferably about 30 min. to about 1.5 hr.

Once the multiple-phase system is established, one phase will be enriched in the polypeptide and depleted in the disrupted particles and cells comprising the biomass solids and nucleic acids. In a two-phase system, preferably the top phase is enriched in the polypeptide whereas the bottom phase is enriched in the disrupted particles and cells. The polypeptide can be easily recovered by separation of the phases. This recovery step may be accomplished by decanting the upper phase, by draining the lower phase, or by centrifugation. The polypeptide can then be isolated from the phase in which it is contained by changing the pH of the phase so as to precipitate the polypeptide or by adding a suitable solvent, whereupon the precipitated polypeptide is suitably recovered by centrifugation or filtration or as a slurry. Alternatively, the polypeptide can be recovered from the polymer-containing phase by re-extraction by addition of a suitable polymer, salt, or solvent. The DsbC protein may also be separated from the recombinant tPA or PTI polypeptide at this stage.

Once obtained from the liquid phase of the multiple-phase system, or at a later stage of purification, the polypeptide may be suitably stored in an appropriate buffer. The buffer can be any buffer known to those of skill in the art to preserve the biological activity and integrity of the isolated recombinant polypeptide. Such buffers include those listed below in Section 5, or alternatively, CAPSO, glycine, CAPS, MOPS, HEPES, etc. may be employed preferably at a pH of from between about pH6 and pH 11, particularly at a concentration of about 20 mM. The polypeptide may be diluted with the buffer, or alternatively, the polypeptide may be dialyzed against fresh buffer.

5. EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

5.1 Example 1

Methods for the Production of Active TPA in *E. coli*

The present example demonstrates the expression of correctly folded, full-length tPA in *E. coli*. It is shown that engineering the disulfide bond machinery of the cell through the high level expression of DsbC allows the production of active tPA in the mg/l scale. This is the first time tPA, or for that matter any eukaryotic protein with more than four disulfide bonds, has been expressed in correctly folded form in bacteria in significant amounts. The development of this system for the expression of a protein as complex as tPA provides a remarkable advance in the area of protein chemistry and provides for the first time the ability to produce complex multidisulfide proteins in bacteria.

5.1.1 Materials and Methods 5.1.1.1 Vector Construction pAP-stII-tPA is a pBR322 derivative containing the tPA gene fused in-frame to the heat stable enterotoxin (stII) leader peptide and placed downstream from the PhoA promoter (Genentech plasmid collection). pBAD-stII-tPA was constructed by amplifying the tPA gene from pAP-stII-tPA with the following primers:

5'-CGCGCGATATCATGAAAAAGAATATCGCATTT-CTTCTT-3' (SEQ ID NO:12) and

5'-TCTACGCAAAGCTTTCACGCTGGTCGCATGTT-GTCA-3' (SEQ ID NO: 13).

The PCR™ product was digested with EcoRI and HindIII and subcloned into pBAD33. pTrc-stII-tPA184 is a pACYC184 derivative in which the tPA gene with the stII leader peptide was placed downstream from the strong $P_{trc}$ promoter from pTrc-99.

pSE380dsbA is a derivative of pSE380 (Invitrogen, Calif.) expressing the dsbA gene from the strong $P_{trc}$ promoter and was obtained from Dr. Kristine De Sutter, University of Ghent. pSE420dsbC is a derivative of pSE420 (Invitrogen, Calif.) expressing the dsbC gene and was obtained from Dr. Satish Raina, Centre Medical Universitaire, Geneva. The vector pSE420dsbAC was constructed as follows: pSE420dsbC was digested with MluI, blunt-ended using Mung Bean Nuclease and further digested with HindIII. Subsequently, the fragment containing the dsbC gene downstream from the $P_{trc}$ promoter was isolated and ligated with StuI/HindIII-treated pSE380dsbA to give pSE380dsbAC.

5.1.1.2 Expression of TPA in Shake Flasks

To evaluate tPA expression in shake flasks, *E. coli* SF110 cells transformed with the appropriate plasmids were grown in LB media supplemented with ampicillin (100 µg/ml), chloramphenicol (20 µg/ml), or kanamycin (40 µg/ml) as necessary. Synthesis of DsbA, DsbC or DsbA+DsbC in cells carrying pSE380dsbA, pSE420dsbC or pSE380dsbAC respectively, was induced by the addition of IPTG (2 mM final concentration) when the culture $O.D._{600}$ reached between 0.8 to 1.0. Synthesis of rPDI in cells transformed with pLpplacOmpArPDI was induced by the addition of IPTG to 0.5 mM at a culture $O.D._{600}$ around 0.6. Expression of tPA from the $P_{BAD}$ promoter was induced 30 min after the addition of IPTG by adding arabinose to a final concentration of 0.2% (wt./vol.).

Following induction with arabinose, cultures were grown for an additional 3 hr and harvested by centrifugation. The cells were then resuspended in 0.1 M Tris-HCl pH 8.5, and lysed with a French pressure cell operated at 20,000 psi. Subsequently, the cell lysates were centrifuged at 12,000× g for 10 min at 4° C. to separate the soluble and insoluble fractions.

5.1.1.3 General Methods

Protein concentrations were determined by the Bradford method with bovine serum albumin as a standard. SDS-PAGE on 12% polyacrylamide gels and Western blotting were performed according to standard techniques (Ausubel et al., 1987). Glycosylated, single chain tPA (Sigma Chemical Co., St. Louis, Mo.) was used as a standard.

5.1.1.4 Immunological Characterization of TPA

Goat polyclonal antibodies were raised against purified recombinant tPA from CHO cells. The mouse monoclonal antibody #365 (mAb 365)recognizes a conformational epitope in the kringle 2 domain. mAb 623 recognizes a conformational epitope in the protease domain (Sehl et al., 1996). All antibodies were obtained from Genentech, Inc.

Sandwich ELISAs were performed as follows: Cells pellets were resuspended in buffer (32 mM $Na_2CO_3$/68 mM $NaHCO_3$), lysed with a French press and aliquots of the soluble fraction were used to coat microtiter plates by incubation overnight at 4° C. The plates were washed three times with washing buffer (0.5% Tween-20® in phosphate buffer saline, PBS) and blocked with 2.5% BSA in PBS at 37° C. for 1 hr. Subsequently, the plates were incubated with antibodies conjugated to horseradish peroxidase (HRP). The antibody-HRP conjugates were prepared using EZ-link™ maleimide activated horseradish peroxidase kit from PIERCE. Following incubation with the appropriate antibody-HRP conjugate, the plates were washed and developed using the HRP substrate kit (Bio-Rad, Hercules, Calif.).

The immunochemical reactivity of the bacterial expressed tPA was determined by capture ELISA (Simmons and Yansura, 1996). Microtiter well plates were coated with different antibodies (capture antibody). Bound tPA with correctly folded conformational epitopes was detected with the appropriate Mab-HRP conjugate.

5.1.1.5 TPA Activity Assay

A fibrin plate activity assay was used for the qualitative determination of fibrin-stimulated activation of plasminogen by tPA. Fibrin plates were prepared essentially as described (Waldenström et al., 1991) except that 25 µg/ml of tetracycline was added to prevent bacterial growth. Cell lysates containing 10 µg protein were spotted on the plates and the development of clearance zones was monitored. The rate of plasminogen activation was determined using SPECTROL-YSE® Tpa/pai Activity Assay Kit (American Diagnostica, Inc., Greenwich, Conn.) using a total assay volume of 295 pi. The amount of active tPA produced in *E. coli* was estimated using the specific activity of the glycosylated, single chain tPA which is 400 IU/µg. Zymography was performed as described (Huessen and Dowdle, 1980) with the following modifications: SDS-12% polyacrylamide gel were copolymerized with 0.1% (wt./vol.) α-casein and 10 µg/ml plasminogen (Calbiochem, San Diego, Calif.). After electrophoresis at 4° C., the gels were washed with 2.5% Triton X-100® for 1 hr to remove the SDS, washed with distilled water exhaustively to remove the Triton X-100®, incubated in 0.1M glycine buffer (pH 8.3) for 5 h and stained.

5.1.2 Results 5.1.2.1 TPA Expression in Shake Flasks

A cDNA encoding the complete amino acid sequence (amino acids 1–527) of the human tPA was fused in-frame to the StII leader peptide which has been shown earlier to be useful for the periplasmic expression of a variety of proteins (Simmons and Yansura, 1996). Studies established that the stII leader peptide is capable of directing the translocation of tPA into the periplasmic space. The stII-tPA gene was placed downstream from three different promoters: the arabinose inducible promoter $P_{BAD}$ (Guzman et al., 1995), the phoA promoter which is transcribed constitutively at a moderate level in phoT mutant cells grown in high phosphate media and, finally, the IPTG-inducible $P_{trc}$ promoter. The respective expression vectors were transformed in several different *E. coli* strains. In every case, a band corresponding to full-length tPA could be detected by Western blotting although, as might be expected, the intensity of tPA band varied considerably depending on the promoter and the strain background. However, no plasminogenolytic activity on fibrin plates were detected, even when up to 10 µg of cell lysate were spotted on the fibrinolytic plate. The sensitivity of the fibrin plate assay is very high; less than 0.005 ng of purified tPA gave a visible falo after prolonged incubation.

Representative results from cells transformed with pBAD-stII-tPA, a low copy plasmid vector (pACYC 177 derivative) containing the stII-tPA gene expressed under the arabinose-inducible $P_{BAD}$ promoter, are shown in FIG. 1A, FIG. 1B, FIG. 1C and FIG. 1D. In these cells the level of tPA as measured by ELISA corresponds to approximately 0.5% of the total cell protein. Cell fractionation demonstrated that the majority (>70%) of the tPA was present in the soluble fraction. Thus, it can be concluded that tPA secreted via the stII leader peptide accumulates in a soluble yet misfolded and inactive form.

It was found earlier that under certain conditions, the co-expression of the rat PDI secreted in the periplasmic space increased the expression of BPTI, a small eukaryotic protein with three disulfide bonds, by up to 15-fold (Ostermeier et al., 1996). Therefore, it was of interest to determine whether periplasmic rPDI can also facilitate the production of active tPA. Strain SF110 (Baneyx and Georgiou, 1990) was used for these and all subsequent studies because: (i) It lacks OmpT and DegP, two of the most active proteases involved in the degradation of secreted proteins; (ii) Since OmpT is a bacterial plasminogen activator, ompT+ cells can exhibit a weak background activity which may interfere with tPA detection. (iii) SF110 cells co-transformed with compatible vectors expressing stII-htPA and various cysteine oxidoreductases were found to have consistently higher fibrinolytic activities both in shake flasks and in fermenters. SF110 was transformed with the plasmid pLpplacOmpArPDI which contains the rPDI fused to an OmpA leader peptide downstream from the strong lpp-lac promoter. rPDI is secreted efficiently into the periplasmic space and upon addition with IPTG it becomes the most abundant protein in the soluble fraction (FIG. 2). A small yet detectable clearance was observed when stII-tPA was expressed from the $P_{BAD}$ promoter (FIG. 1A). However, active tPA was barely detectable in a quantitative assay that measures the rate of activation of plasminogen with a chromogenic substrate (FIG. 1B). Also, no clearance zone at the appropriate molecular weight could be detected by Zymography. The low levels of tPA activity were not due to poor expression of the stII-tPA; even though co-expression of rPDI reduced the accumulation of stII-tPA relative to control cells (pBAD-stII-tPA plasmid alone) a band corresponding to mature tPA was readily visible by Western blotting.

pSE380dsbA and pSE420dsbC are pBR322 derivatives expressing the soluble periplasmic cysteine oxidoreductases DsbA and DsbC, respectively, under the control of the IPTG inducible $P_{trc}$ promoter. To test the effect of DsbA and/or DsbC overproduction on the formation of correctly folded tPA, the latter was expressed from pBAD-stII-tPA. In this way the synthesis of DsbA and/or DsbC could be induced with IPTG whereas synthesis of stII-tPA could be controlled independently through the addition of arabinose. Induced cultures carrying pSE380dsbA or pSE420dsbC, expressed DsbA and DsbC respectively at a high level. DsbA accumulated exclusively as the mature, periplasmic form, whereas overexpression of DsbC resulted in the appearance of a higher molecular weight band corresponding to the precursor form of the protein (FIG. 2). The level of expression of tPA, was detected by Western blotting, was not affected by the coexpression of DsbA, DsbC or DsbA+DsbC (FIG. 1D).

The co-expression of high levels of DsbC resulted in a dramatic increase in plasminogen activation (FIG. 1A, FIG. 1B, FIG. 1C and FIG. 1D). Zymography revealed that this activity arose from a band with electrophoretic mobility slightly less than that of the single chain tPA standard. This is consistent with the fact that the tPA standard is glycosylated whereas the bacterial protein is not. No other bands were detectable in Zymography gels (FIG. 1C) indicating that the activity observed on fibrin plates and with the SPECTROLYSE™ assay must arise from the full-length protein and not from degradation products. Manipulation of the redox environment through the addition of GSH and/or GSSG was also detrimental in cultures co-expressing DsbC and stII-tPA. The presence of as little as 0.5 mM GSSG resulted in over a 40-fold lower specific activities (FIG. 3). Similarly, no further increase in the activity of tPA per unit protein was seen when the origins of replication and the promoters in pBAD-stII-tPA and pSE420dsbC were interchanged.

5.2 Example 2 tPA Expression in High-Cell-Density Fermentations

SF110 (pBAD-stII-tPA+pSE420dsbC) cells were grown in a 10-liter fermenter in a synthetic medium supplemented with leucine and casein amino acids. The growth rate was maintained at 0.4 hr-1 by controlling the addition of glucose to maintain a constant dissolved oxygen level. Studies revealed that induction of DsbC expression leads to a dramatic reduction in the oxygen uptake rate after about 1.5 hr. Growth ceased and a slow decline in the optical density of the culture soon followed. Therefore, a lower concentration of IPTG (0.05 mM) was used to minimize the detrimental effects of DsbC overexpression. IPTG was added when the culture reached an $OD_{600}$ of around 80, followed by a bollus of arabinose 30 min later. Under these conditions the oxygen uptake rate remained constant for 3.5 hr and then begun to decline. The maximum specific tPA activity was attained 2.5 hr after induction (FIG. 4). However, 3 hr later it had decreased by more than 4-fold. The maximum concentration of tPA in the fermenter, on the basis of the protease activity was over 1 mg/l.

TABLE 2

TPA EXPRESSION IN VARIOUS *E. COLI* HOSTS

| Bacterial Strains | Genotype | Activity[1] |
|---|---|---|
| SF110 | F' ΔlacX74 galK thi rpsL(slrA) ΔphoA (PvuII)degP41 (ΔPstI)::Ω Kan[R] Δ(ompT-entF) | ++++[2] |
| SF100 | F' ΔlacX74 galK thi rpsL(strA) ΔphoA (PvuII)Δ (ompT – eutF) | ++++ |
| SF310 | F-, araD139, Δ (lac)u169, febB5301, deoC1, ptsF25, relA1, rbsL, rpsL*, thiA, htpR15 (mini tet nearby) degP41 (ΔPstI – KanR) | ++++ |
| JCB570 | Δ(lacIPOZYA)X74 phoR zih12::Tn10 | ++++ |

TABLE 2-continued

TPA EXPRESSION IN VARIOUS *E. COLI* HOSTS

| Bacterial Strains | Genotype | Activity[1] |
|---|---|---|
| 48A3 | *E. coli* W3110 tonA phoA Δ(argF-lac) ptr3 degP Kan[S] ompT ilu6[+] ara714 | +[3] |
| 27H1 | W3110 tonA tolA phoT459 pabA1 | + |

[1]active tPA level when co-expressed with pSE420dsbC in each strain
[2]++++ indicates the active tPA level is about $1 \times 10^{-2}$ I.U./μg soluble protein
[3]+ indicates the active tPA level is at most $1 \times 10^{-3}$ I.U./μg soluble protein

5.3 Example 3

Effects of Co-Expression of DSBD, DSBE or DSBF on tPA Yield

Recent genetic studies have identified three genes that play a role in the formation of disulfide bonds in the periplasmic space. These genes have been designated dsbD, dsbE, and dsbF. DsbD is a 53 kDa membrane protein with a large thioredoxin like domain which can be expressed without the transmembrane part and is active as an oxidoreductase (Missiakas et al., 1995). DsbE is a soluble protein whereas DsbF is membrane bound. DsbE and DsbF are involved in disulfide bond formation in the periplasmic space although their exact function is not known. The studies below are designed to test whether overexpression of DsbD, DsbE or DsbF can enhance the yield of correctly folded tPA.

Plasmids were constructed to overexpress DsbD, DsbE or DsbF in bacteria. These plasmids were based on the expression vector pTrc-99 (Invitrogen, Carlsbad, Calif.). For the construction of pTrc-dsbD, pTrc-dsbE and pTrc-dsbF, dsbD gene was PCR™ amplified from genomic DNA using the primers:
5'-AGGAATTCAGGAGGTCTCGCATGCAGCTGCCG- CAAGGCGTCTGGCA-3' (SEQ ID NO: 1), and
5'-ACGGGATCCAAGCTTCACGGTTGGCGATCGCG- CAAATGTG-3' (SEQ ID NO:2).

The start codon of the dsbD gene was changed from the native GTG to ATG. The PCR™ product was digested with BsaI and HindIII and subcloned into NcoI/HindIII digested pTrc-99A. The dsbE gene was PCR™ amplified from pSR2241 using the primers:
5'-CGGAATTCTCATGAAGCGCAAAGTATTGTTAA- TTC-3' (SEQ ID NO:3), and
5'-ACGGGATCCAAGCTTCATTGTGCGGCCTCCTTA-3' (SEQ ID NO:4).

The PCR™ product was digested with RcaI and HindIII and subcloned into NcoI/HindIII digested pTrc-99A. The dsbF gene was PCR™ amplified from pSR3285 (obtained from S. Raina) and the PCR™ product was digested with NcoI and HindIII and subcloned into NcoI/HindIII digested pTrc-99A. The following primers were used:
5'-CGGAATTCCCATGGTGAAAAAAGCGATAGTGAC- 3' (SEQ ID NO:5), and
5'-ACGGGATCCAAGCTTTACTGCCCCAAACTACTG- AA-3' (SEQ ID NO:6).

The effect of DsbD, DsbE or DsbF overexpression on the yield of active tPA was evaluated as follows: *E. coli* SF110 cells were transformed with pBAD-stII-tPA and either pTrc-dsbD, pTrc-dsbE or pTrc-dsbF as appropriate. *E. coli* SF110 cells were transformed with pBAD-stII-tPA and either pTrc-dsbD, pTrc-dsbE or pTrc-dsbF as appropriate. The cells were grown in LB media supplemented with ampicillin (100

μg/ml), or chloramphenicol (20 μg/ml), as necessary. Synthesis of DsbD, DsbE or DsbF in cells carrying pTrc-dsbD, pTrc-dsbE or pTrc-dsbF respectively was induced by the addition of IPTG (0.5 mM final concentration) when the culture $O.D._{600}$ reached 0.6. Expression of tPA from the $P_{BAD}$ promoter was induced 30 min. after the addition of IPTG by adding arabinose to a final concentration of 0.2%.

Following induction with arabinose, cultures were grown for an additional 3 hr and harvested by centrifugation. The cells were then resuspended in Tris-HCl buffer (100 mM, pH 8.5), and lysed with a French pressure cell operated at 20,000 psi. Subsequently the cell lysates were centrifuged at 12,000× g for 10 min. at 4° C. to separate the soluble and insoluble fractions. A fibrin plate activity assay was used for the qualitative determination of fibrin-stimulated activation of plasminogen by tPA. However, tPA activity was not observed. Overexpression of either DsbD, DsbE or DsbF in cells grown in different redox environments failed to give rise to any active tPA.

5.4 Example 4

DsBC Overexpression and the Production of Truncated tPA Variants

Recent studies have shown that tPA deletion mutants lacking the finger domain and/or the epidermal growth factor domain and the kringle 1 domain may have improved pharmacokinetic properties. In fact clinical studies are currently underway to test efficacy of truncated tPA variants. The following studies describe experimental protocols for the production of tPA deletion mutants in bacteria through the engineering of the disulfide bond apparatus of E. coli in a manner analogous to what is described in the specification.

Table 3 outlines the salient characteristics of several expression vectors for tPA variants.

TABLE 3

CONSTRUCTION OF
EXPRESSION SYSTEMS FOR TPA VARIANTS

| Construct | Promoter | Signal Sequence | Origin |
|---|---|---|---|
| pTrc-stII-vt-tPA | $P_{trc}$ | StII | pBR322 |
| pTrc-OmpA-vt-tPA | $P_{trc}$ | OmpA | pBR322 |
| pLpp-OmpA-vt-tPA | $P_{lpp-lac}$ | OmpA | pBR322 |
| pBAD33-StII-vt-tPA | $P_{ara}$ | StII | pBR322 |
| pTrc-StII-vt-tPA184 | $P_{trc}$ | StII | pACYC184 |

In the above plasmid vectors, the designation "vt-tPA" corresponds to the desired tPA deletion mutant. All vectors were constructed starting from the corresponding plasmids expressing full length tPA as described elsewhere in Section 5. Deletions of the finger domain, growth factor-like domain or kringle 1 domain were constructed using Quantum LeapTM Nested Deletion Kit (Clontech, Palo Alto, Calif.) with the following deletion primer:
5'-CGCGTACGCTTATGCAAGATCTTACCAAGTGATC-GGAAACAGTGACTGCTACTTTGGGAATGGG-3' (SEQ ID NO: 7)

pLppsOmpA-vt-tPA was constructed by inserting tPA variant kringle-2-protease amplified from pAP-stII-tPA using the deletion primer (see above) and a backward primer into pINIII-OmpA1 (Ghrayeb et al., 1984) linearized by BamHI.

SF110 was transformed with plasmid vectors expressing a deletion mutant of tPA from the list shown above and with pSE420dsbC. The cells are grown in LB media and induced with IPTG and arabinose as described elsewhere in Section 5. tPA activity is measured using the fibrin plate assay and quantified using the chromogenic substrate assay as described herein.

5.5 Example 5

Identification and Characterization of DsBG

A basic BLAST search was conducted comparing the 236 amino acid sequence of E. coli DsbC against all non-redundant protein sequences in the databases GenBank CDS translations, PDB, SwisProt, and PIR. A 268 amino acid open reading frame in the E. coli genome was identified bearing 30% identity to the protein query, with 36% identity, 57% homology (allowing for conservative substitutions) in the 19 amino acid window surrounding the DsbC active site. Furthermore, the hypothetical protein identified contained the thioredoxin-like Cys-X-X-Cys motif found in all known members of the dsb gene family. The nucleotide sequence for this open reading frame is found in GenBank accession number AE000166, corresponding to approximately 13.8 minutes on the E. coli genome map and located on the complement strand.

The complete 268 amino acid coding sequence was amplified by PCR™ from template DNA purified from Kohara phage #166 using the primers:

5'-AAGCTCTTACTCATGACAGTGATAGGTTATGC-3' (SEQ ID NO:8) and

5'-CCATCCATGAGGATCCTTTTATTTATTCCCCAT-AAT-3' (SEQ ID NO:9).

The resulting product was digested with restriction enzymes RcaI and BamHI and ligated into expression vector pTrc99A (Pharmacia, Uppsala, Sweden), previously digested with NcoI and BamHI, downstream of the trc promoter generating pTrcdsbG. The N-terminal junction was confirmed by automated DNA sequencing. pETdsbGhis was constructed by amplifying the dsbG without its stop codon using pTrcdsbG as template and SEQ ID NO:8 and SEQ ID NO:9 as primers:

The PCR™ product was digested with RcaI and XhoI and ligated into the expression vector pET28a (Novagen, Madison, Wis.) which had been cleaved with NcoI and XhoI. The resulting plasmid contains the coding sequence for DsbG, fused to a 6X Histidine tag at its C-terminus, under the control of the T7 promoter.

pETdsbGhis was transformed into strain BL21(DE3), and the resulting strain was used for purification of DsbG. A culture in LB media supplemented with 50 μg/ml kanamycin was induced with 0.5 mM IPTG at $OD_{600}$=0.6; after 3 hours, the cells were harvested, and the periplasmic contents were isolated by osmotic shock. Histidine tagged DsbG was purified from the osmotic shockate using Ni-chelate chromatography, following standard protocols (Novagen, Madison, Wis.). The column eluate was visualized by SDS-PAGE followed by Coomassie staining and found to be approximately 99% pure. N-terminal peptide sequencing of the mature periplasmic protein revealed the signal peptidase cleavage site after Ala 37.

The following strains were co-transformed with a plasmid expressing bovine pancreatic trypsin inhibitor (BPTI) and either pTrcdsbG or a control plasmid: R189 (MC1000 phoR Δara714leu⁺), RI179 (RI89 dsbC::Cm), RI242 (RI89 dsbD::Cm), MC4100, SR3324 (MC4100 htrA-lacZ⁺ dsbC::Kan). The resulting strains were grown in minimal media supplemented with glucose, casein hydrolysate, and the appropriate antibiotics, induced with 1.0 mM IPTG at OD600=0.3, and harvested five hours later. The cultures were lysed by French pressure cell, and the soluble fractions were analyzed for BPTI expression by ELISA. In other studies with E. coli, SF110 was cotransformed with pBAD-stII-tpA3 and pTrcdsbG. Cells were grown in LB media and induced with 2 mM IPTG and 1% arabinose. The tPA activity was measured 5 h later. Cells not containing pTrcdsbG had no tPA activity. In contrast, cells containing both plasmids had tPA activity equal to 0.5 U/mg (uninduced) and 2 U/mg (induced).

5.6 EXAMPLE 6 -- DNA SEQUENCE OF THE DSBG GENE (SEQ ID NO:10)

```
ATGACAGTGATAGGTTATGCCTTTTACTCGACTTTTGCACTGACTGAAAAGGACAAA

TTAATGTTAAAAAAGATACTTTTACTGGCTCTGCTTCCTGCAATCGCCTTCGCAGAG

GAACTTCCTGCTCCAGTAAAAGCGATTGAAAAACAGGGCATTACAATCATCAAAACA

TTCGATGCCCCCGGAGGAATGAAAGGTTATCTCGGAAAGTATCAGGATATGGGCGTC

ACCATCTACCTGACTCCACATGGTAAGCACGCTATCTCTGGTTACATGTACAACGAG

AAAGGTGAAAACCTGAGTAACACACTTATCGAAAAAGAAATTTACGCACCAGCCGGA

CGCGAAATGTGGCAACGGATGGAACAATCCCACTGGCTCCTCGACGGTAAAAAAGAT

GCGCCGGTCATTGTCTACGTCTTCGCCGATCCGTTCTGCCCATATTGTAAACAGTTC

TGGCAGCAGGCGCGCCCGTGGGTAGATTCTGGCAAAGTGCAATTAAGAACATTGTTG

GTTGGGGTTATCAAGCCAGAAAGCCCGGCGACAGCAGCGGCAATTCTTGCCTCCAAA

GATCCCGCAAAAACCTGGCAACAATATGAAGCCTCTGGTGGCAAGCTTAAGCTAAAC

GTGCCTGCAAACGTAAGTACAGAGCAAATGAAAGTGTTAAGTGACAATGAGAAACTG

ATGGACGATCTGGGGGCAAATGTCACGCCGGCTATCTATTACATGAGTAAGGAAAAT

ACGCTACAACAGGCCGTGGGGTTGCCCGATCAGAAAACGCTTAATATCATTATGGGG

AATAAATAA
```

5.7 EXAMPLE 7 -- AMINO SEQUENCE OF THE $D_{SB}G$ PROTEIN (SEQ ID NO:11)

```
MTVIGYAFYSTFALTEKDKLMLKKILLLALLPAIAFAEELPAPVKAIEKQGITIIKTF

DAPGGMKGYLGKYQDMGVTIYLTPDGKHAISGYMYNEKGENLSNTLIEKEIYAPAGRE

MWQRMEQSHWLLDGKKDAPVIVYVFADPFCPYCKQFWQQARPWVDSGKVQLRTLLVGV

IKPESPATAAAILASKDPAKTWQQYEASGGKLKLNVPANVSTEQMKVLSDNEKLMDDL

GANVTPAIYYMSKENTLQQAVGLPDQKTLNIIMGNK
```

6. REFERENCES

The following literature citations as well as those cited above are incorporated in pertinent part by reference herein for the reasons cited in the above text:

U.S. Pat. No. 4,431,740.
U.S. Pat. No. 4,554,101.
U.S. Pat. No. 4,652,525.
U.S. Pat. No. 4,661,453.
U.S. Pat. No. 4,683,195.
U.S. Pat. No. 4,683,202.
U.S. Pat. No. 5,077,392.
U.S. Pat. No. 5,270,181.
U.S. Pat. No. 5,292,646.
U.S. Pat. No. 5,304,472.
U.S. Pat. No. 5,336,602.
U.S. Pat. No. 5,342,763.
U.S. Pat. No. 5,508,192.
Austr. Pat. Appl. AU 61804/86.
Eur. Pat. App. No. EP 024,208.
Eur. Pat. App. No. EP 196,920.
Eur. Pat. App. No. EP 207,589.
Eur. Pat. App. No. EP 231,624.
Eur. Pat. App. No. EP 234,051.
Eur. Pat. App. No. EP 240,334.
Eur. Pat. App. No. EP 263,172.
Eur. Pat. App. No. EP 289,508.
Eur. Pat. App. No. EP 292,009.
Eur. Pat. App. No. EP 293,793.
Eur. Pat. App. No. EP 297,066.
Eur. Pat. App. No. EP 302,456.
Eur. Pat. App. No. EP 304,311.
Eur. Pat. App. No. EP 352,119.
Eur. Pat. App. No. EP 379,890.
Eur. Pat. App. No. EP 382,174.
Eur. Pat. App. No. EP 509,841.
Eur. Pat. App. No. EP 510,658.
Int. Pat. Appl. Publ. No. WO 89/12681.
Int. Pat. Appl. Publ. No. WO 93/25676.
Int. Pat. Appl. Publ. No. WO 93/24635.
Int. Pat. Appl. Publ. No. WO 94/08012.
Int. Pat. Appl. Publ. No. WO 96/14422.
Jap. Pat. Appl. No. JP 60-38771.
Ausubel et al., *Current Protocols in Molecular Biology*, John Wiley and Sons, New York, 1987.
Baneyx and Georgiou, "In vivo degradation of secreted fusion proteins by the *Escherichia coli* outer membrane protease OmpT," *J. Bacteriol.*, 172:491–494, 1990.
Baneyx and Georgiou, In: *Stability of Protein Pharmaceuticals: Chemical and Physical Patterns of Protein Degradation*, (Ahern and Manning, Eds), Plenum Press, New York, pp. 69–96, 1992.
Bardwell and Beckwith, *Cell*, 74:769–771, 1993.
Bardwell et al., "A Pathway for Disulfide Bond Formation In vivo," *Proc. Natl. Acad. Sci. USA*, 90:1–5, 1993A.
Bardwell et al., *Proc. Natl. Acad Sci. USA*, 90:1038–1042, 1993B.
Bardwell, "Building Bridges: Disulphide Bond Formation in the Cell," *Mol. Microbiol.*, 14:199–205, 1994A.
Bardwell, *Molec. Micro.*, 14:199–305, 1994B.

Bolivar et al., *Gene,* 2:95, 1977.

Braig et al., "The Crystal Structure of the Bacterial Chaperonin GroEL at 2.8 Å" *Nature,* 371:578–586, 1994.

Cai et al., "Chaperone-Like Activity of Protein Disulfide Isomerase in the Refolding of a Protein with no Disulfide Bonds," *J. Biol. Chem.,* 269:24550–24552, 1994.

Carteretal., *Nucl. Acids Res.,* 12:4431–4443, 1985.

Chang et al., *Nature,* 375:615, 1978.

Chun et al., *J. Biol. Chem.,* 268:20855–20862, 1993.

Couvreur et al., "Nanocapsules, a New Lysosomotropic Carrier," *FEBS Lett.,* 84:323–326, 1977.

Couvreur, "Polyalkyleyanoacrylates as Colloidal Drug Carriers," *Crit. Rev. Ther. Drug Carrier Syst.,* 5:1–20, 1988.

Creighton and Goldenberg, "Kinetic Role of a Meta-Stable Native-Like Two-Disulfide Species in the Folding Transition of Bovine Pancreatic Trypsin Inhibitor," *J. Mol. Biol.,* 179:497–526, 1984.

Creighton et al., "On the Biosynthesis of Bovine Pancreatic Trypsin Inhibitor (BPTI)," *J. Mol. Biol.,* 232:1176–1196, 1993.

Dailey and Berg, "Mutants in Disulfide Bond Formation that Disrupt Flagellar Assembly in *Escherichia coli,*" *Proc. Natl. Acad. Sci. USA,* 90:1043–1047, 1993.

Darby et al., "Dissecting the Mechanism of Protein Disulfide Isomerase: Catalysis of Disulfide Bond Formation in a Model Peptide," *Biochemistry,* 33:7937–7947, 1994.

De Sutter et al., *Gene,* 141:163–170, 1994.

De Sutter et al., *Mol. Micro.,* 6:2201–2208, 1992.

Fukuzono, Fujimori, Shimizu, "Production of biologically active mature brain-derived neurotrophic factor in *Escherichia coli,*" *Biosci. Biotech. Biochem.,* 59:1727–1731, 1995.

Gabizon and Papahadjopoulos, "Liposomes Formulations with Prolonged Circulation Time in Blood and Enhanced Uptake by Tumors," *Proc. Natl. Acad. Sci. USA,* 85:6949–6953, 1988.

Georgiou and Valax, "Expression of correctly folded proteins in *Escherichia coli,*" *Curr. Op. Biotechnol,* 7:190–7, 1996.

Goeddel et al., *Nature,* 281:544, 1979.

Goeddel et al., *Nucl. Acids Res.,* 8:4057, 1980.

Goldenberg, "Kinetic analysis of the folding and unfolding of a mutant form of bovine pancreatic trypsin inhibitor lacking the cysteine-14 and -38 thiols," *Biochemistry,* 27:2481–2489, 1988.

Goldenberg, "Native and Non-Native Intermediates in the BPTI Folding Pathway," *TIBS,* 17:257–261, 1992.

Grauschopf, Wither, Korber, Zander, Dallinger, Bardwell, "Why is DsbA such an oxidizing disulfide catalyst," *Cell,* 23:947–955, 1995.

Grunfeld, Patel, Shatzman, "Effector-assisted refolding of recombinant tissue-plasminogen activator produced in *Escherichia coli,*" *Appl. Biochem. Biotechnol.,* 33:117–38, 1992.

Guzman et al., "Tight regulation, modulation, and high-level expression by vectors containing the arabinose $P_{BAD}$ promoter," *J. Bacteriol,* 177:4121–30, 1995.

Haigwood et al. *Prot. Engineer.,* 2:611, 1989.

Henry-Michelland et al., "Attachment of Antibiotics to Nanoparticles; Preparation, Drug-Release and Antimicrobial Activity in vitro," *Int. J. Pharm.,* 35:121–127, 1987.

Hess et al., *J. Adv. Enzyme Reg.,* 7:149, 1968.

Hitzeman et al., *J. Biol. Chem.,* 255:2073, 1980.

Hockney, "Recent developments in heterologous protein production in *Escherichia coli,*" *Trends Biotech.,* 12:456–463, 1994.

Hotchkiss et al. *Thromb. Haemost.,* 60:255, 1988.

Huessen and Dowdle, "Electrophoretic analysis of plasminogen activators in polyacrylamide gels containing sodium dodecyl sulfate ad copolymerized substrates," *Anal. Biochem.,* 102:196–202, 1980.

Hultgren et al., "Pilus and Nonpilus Bacterial Adhesins: Assembly and Function in Cell Recognition," *Cell,* 73:887–901, 1993.

Itakura et al., *Science,* 198:1056, 1977.

Jacob-Dubuisson et al., "PapD Chaperone Function in Pilus Biogenesis Depends on Oxidant and Chaperone-Like Activities of DsbA," *Proc. Natl. Acad. Sci. USA,* 91:11552–11556, 1994.

Jander et al., "Two Cysteines in Each Periplasmic Domain of the Membrane Protein DsbB are Required for its Function in Protein Disulfide Bond Formation," *EMBO J.,* 13:5121–5127, 1994.

Jones, *Genetics,* 85:12, 1977.

Kingsman et al., *Gene,* 7:141, 1979.

Kyte and Doolittle, *J. Mol. Biol.,* 157(1):105–132, 1982.

Maloy et al., *"Microbial Genetics,"* 2nd Edition. Jones and Bartlett Publishers, Boston, Mass., 1994.

Maniatis et al., *"Molecular Cloning: a Laboratory Manual,"* Cold Spring Harbor Laboratory, Cold Spring Harbor, N.Y., 1982.

Marks et al., "Production of Native, Correctly Folded Bovine Pancreatic Trypsin Inhibitor by *Escherichia coli,*" *J. Biol. Chem.,* 261:7115–7118, 1986.

Martin et al., "Crystal Structure of the DsbA Protein Required for Disulphide Bond Formatin In vivo," *Nature,* 365:464–468, 1993.

McGrath et al., J. Biol. Chem., 266(10):6620–6625, 1991.

Missiakas et al., "Identification and characterization of a new disulfide isomerase-like protein (DsbD) in *Escherichia coli,*" *EMBO J.,* 14:3415–24, 1995.

Missiakas et al., "Identification and Characterization of the *Escherichia coli* Gene dsbB, Whose Product is Involved in the Formation of Disulfide Bonds In vivo," *Proc. Natl. Acad Sci. USA,* 90:7084–7088, 1993.

Missiakas et al., "The *Escherichia coli* dsbC (xprA) Gene Encodes a Periplasmic Protein Involved in Disulfide Bond Formation," *EMBO J.,* 13:2013–2020, 1994.

Nilsson et al., "Secretion Incompetence of Bovine Pancreatic Trypsin Inhibitor Expressed in *Escherichia coli,*" *J. Biol. Chem.,* 266:2970–2977, 1991.

Novia et al., *J. Biol. Chem.,* 266:19645–19649, 1991.

Ogrydziak, "Yeast extracellular proteases," *CRC Crit. Rev. Biotechnol.,* 13:1–55, 1993.

Ostermeier and Georgiou, "The folding pathway of BPTI in the periplasmic space of *Escherichia coli,*" *J. Biol. Chem.,* 269:21072–21077, 1994.

Ostertneier et al., "The eucaryotic protein disulfide isomerase complements *Escherichia coli* dsbA mutants and increases the yield of heterologous secreted proteins with disulfide bonds," *J. Biol. Chem.,* 271:10616–10622, 1996.

Pollitt and Zalkin, *J. Bacteriol.,* 153:27–32, 1983.

Prokop and Bajpai, In: *Recombinant DNA Technology I,* Ann. N.Y. Acad. Sci., Vol. 646, 1991.

Raj et al. *Biochemistry,* 28:7644–7662, 1989.

Rijken et al. *J. Biol. Chem.,* 256:7035, 1981.

Rudolph and Lilie, "In vitro folding of inclusion body proteins," i FASEB J., 50:49–56, 1996.

Sambrook et al., In: *Molecular Cloning: A Laboratory Manual,* 2nd Edition, Chapter 12.6, Cold Spring Harbor Laboratory, Cold Spring Harbor, N.Y., 1989.

Segal, In: *Biochemical Calculations,* 2nd Edition, John Wiley and Sons, New York, 1976.

Sehl, Nguyen, Berleau, Arcila, Bennett, Keyt, "Locating the unpaired cysteine of tissue plasminogen activator," *Prot. Eng.,* 9:283–290, 1996.

Shevchik et al., "Characterization of DsbC, a Periplasmic Protein of *Erwinia chrysanthemi* and *Escherichia coli* with Disulfide Isomerase Activity," *EMBO J.,* 13:2007–2012, 1994.

Silhavy et al., In: *Studies with Gene Fusions,* Cold Spring Harbor Laboratory, Cold Spring Harbor, N.Y., 1983.

Simmons and Yansura, "Translational level is a critical factor for the secretion of heterologous proteins in *Escherichia coli,"* Nature Biotechnol., 14:629–634, 1996.

Spellman et al. *J. Biol. Chem.,* 264(24):14100–14111, 1989.

Stinchcomb et al., *Nature,* 282:39, 1979.

Tschemper et al., *Gene,* 10:157, 1980.

Van Mierlo et al., "Partially Folded Conformation of the (30–51) Intermediate in the Disulphide Folding Pathway of Bovine Pancreatic Trypsin Inhibitor," *J. Mol. Biol.,* 229:1125–1146, 1993.

Verheijen et al. *EMBO J.,* 5:3525–30, 1986.

Vincent and Lazdunski, *Biochemistry,* 11:2967–2977, 1972.

Waldenström, Holmgren, Attersand, Kalderen, Löwenadler, Raden, Hansson, Pohl, "Synthesis and secretion of a fibrinolytically active tissue plasminogen activator variant in *Escherichia coli,"* Gene, 99:243–248, 1991.

Walker and Gilbert, "Effect of redox environment on the in vitro and in vivo folding of RTEM-1 β-Lactamase and *E. coli* alkaline phosphatase," *J. Biol. Chem.,* 269:28487–93, 1994.

Weissman and Kim, "Efficient Catalysis of Disulphide Bond Rearrangement by Protein Disulphide Isomerase," *Nature,* 365:185–188, 1993.

Weissman and Kim, "Kinetic Role of Nonnative Species in the Folding of Bovine Pancreatic Trypsin Inhibitor," *Proc. Natl. Acad. Sci. USA,* 89:9900–9904, 1992.

Weissman and Kim, "Reexamination of the Folding of BPTI: Predominance of Native Intermediates," *Science,* 253:1386–1393, 1991.

Wittrup, "Disulfide bond formation and eukaryotic secretory productivity," *Curr. Opin. Biotech.,* 6:203–208, 1995.

Wuilfing and Plückthun, "Protein folding in the periplasm of *Escherichia coli,"* Mol. Microbiol, 12:685–692, 1994.

Wunderlich et al., "Bacterial Protein Disulfide Isomerase: Efficient Catalysis of Oxidative Protein folding at Acidic pH," *Biochemistry,* 32:12251–12256, 1993.

Zapun and Creighton, "Effects of DsbA on the Disulfide Folding of Bovine Pancreatic Trypsin Inhibitor and β-Lactalbumin," *Biochemistry,* 33:5202–5211, 1994.

Zapun et al., "Folding in vitro of Bovine Pancreatic Trypsin Inhibitor in the Presence of Proteins of the Endoplasmic Reticulum," *Proteins: Structure, Function, and Genetics,* 14:10–15, 1992.

Zapun et al., "Replacement of the Active-Site Cysteine Residues of DsbA, a Protein Required for Disulfide Bond Formation In vivo," *Biochemistry,* 33:1907–1914, 1994.

Zapun et al., "The Reactive and Destabilizing Disulfide Bond of DsbA, a Protein Required for Protein Disulfide Bond Formation In vivo," *Biochemistry,* 32:5083–5092, 1993.

---

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (xi) SEQUENCE DESCRIPTION: SEQ ID NO:1:

AGGAATTCAG GAGGTCTCGC ATGCAGCTGC CGCAAGGCGT CTGGCA        46

(2) INFORMATION FOR SEQ ID NO:2:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:2:

ACGGGATCCA AGCTTCACGG TTGGCGATCG CGCAAATGTG        40

(2) INFORMATION FOR SEQ ID NO:3:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:3:

CGGAATTCTC ATGAAGCGCA AAGTATTGTT AATTC                                       35

(2) INFORMATION FOR SEQ ID NO:4:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:4:

ACGGGATCCA AGCTTCATTG TGCGGCCTCC TTA                                         33

(2) INFORMATION FOR SEQ ID NO:5:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:5:

CGGAATTCCC ATGGTGAAAA AAGCGATAGT GAC                                         33

(2) INFORMATION FOR SEQ ID NO:6:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:6:

ACGGGATCCA AGCTTTACTG CCCCAAACTA CTGCAA                                      36

(2) INFORMATION FOR SEQ ID NO:7:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (xi) SEQUENCE DESCRIPTION: SEQ ID NO:7:

CGCGTACGCT TATGCAAGAT CTTACCAAGT GATCGGAAAC AGTGACTGCT ACTTTGGGAA            60

TGGG                                                                         64

(2) INFORMATION FOR SEQ ID NO:8:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:8:

AAGCTCTTAC TCATGACAGT GATAGGTTAT GC                                          32

(2) INFORMATION FOR SEQ ID NO:9:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:9:

CCATCCATGA GGATCCTTTT ATTTATTCCC CATAAT                                36

(2) INFORMATION FOR SEQ ID NO:10:

(i) SEQUENCE CHARACTERISTICS:
       (A) LENGTH: 807 base pairs
       (B) TYPE: nucleic acid
       (C) STRANDEDNESS: single
       (D) TOPOLOGY: linear (xi) SEQUENCE DESCRIPTION: SEQ ID NO:10:

ATGACAGTGA TAGGTTATGC CTTTTACTCG ACTTTTGCAC TGACTGAAAA GGACAAATTA      60

ATGTTAAAAA AGATACTTTT ACTGGCTCTG CTTCCTGCAA TCGCCTTCGC AGAGGAACTT     120

CCTGCTCCAG TAAAAGCGAT TGAAAAACAG GGCATTACAA TCATCAAAAC ATTCGATGCC     180

CCCGGAGGAA TGAAAGGTTA TCTCGGAAAG TATCAGGATA TGGGCGTCAC CATCTACCTG     240

ACTCCAGATG GTAAGCACGC TATCTCTGGT TACATGTACA ACGAGAAAGG TGAAAACCTG     300

AGTAACACAC TTATCGAAAA AGAAATTTAC GCACCAGCCG GACGCGAAAT GTGGCAACGG     360

ATGGAACAAT CCCACTGGCT CCTCGACGGT AAAAAAGATG CGCCGGTCAT TGTCTACGTC     420

TTCGCCGATC CGTTCTGCCC ATATTGTAAA CAGTTCTGGC AGCAGGCGCG CCCGTGGGTA     480

GATTCTGGCA AAGTGCAATT AAGAACATTG TTGGTTGGGG TTATCAAGCC AGAAAGCCCG     540

GCGACAGCAG CGGCAATTCT TGCCTCCAAA GATCCCGCAA AAACCTGGCA ACAATATGAA     600

GCCTCTGGTG GCAAGCTTAA GCTAAACGTG CCTGCAAACG TAAGTACAGA GCAAATGAAA     660

GTGTTAAGTG ACAATGAGAA ACTGATGGAC GATCTGGGGG CAAATGTCAC GCCGGCTATC     720

TATTACATGA GTAAGGAAAA TACGCTACAA CAGGCCGTGG GGTTGCCCGA TCAGAAAACG     780

CTTAATATCA TTATGGGGAA TAAATAA                                        807

(2) INFORMATION FOR SEQ ID NO:11:

(i) SEQUENCE CHARACTERISTICS:
       (A) LENGTH: 268 amino acids
       (B) TYPE: amino acid
       (C) STRANDEDNESS:
       (D) TOPOLOGY: linear (xi) SEQUENCE DESCRIPTION: SEQ ID NO:11:

Met Thr Val Ile Gly Tyr Ala Phe Tyr Ser Thr Phe Ala Leu Thr Glu
1               5                   10                  15

Lys Asp Lys Leu Met Leu Lys Lys Ile Leu Leu Ala Leu Leu Pro
            20                  25                  30

Ala Ile Ala Phe Ala Glu Glu Leu Pro Ala Pro Val Lys Ala Ile Glu
        35                  40                  45

Lys Gln Gly Ile Thr Ile Ile Lys Thr Phe Asp Ala Pro Gly Gly Met
    50                  55                  60

Lys Gly Tyr Leu Gly Lys Tyr Gln Asp Met Gly Val Thr Ile Tyr Leu
65                  70                  75                  80

Thr Pro Asp Gly Lys His Ala Ile Ser Gly Tyr Met Tyr Asn Glu Lys
                85                  90                  95

Gly Glu Asn Leu Ser Asn Thr Leu Ile Glu Lys Glu Ile Tyr Ala Pro
            100                 105                 110

Ala Gly Arg Glu Met Trp Gln Arg Met Glu Gln Ser His Trp Leu Leu
        115                 120                 125

```
Asp Gly Lys Lys Asp Ala Pro Val Ile Val Tyr Val Phe Ala Asp Pro
        130                 135                 140

Phe Cys Pro Tyr Cys Lys Gln Phe Trp Gln Gln Ala Arg Pro Trp Val
145                 150                 155                 160

Asp Ser Gly Lys Val Gln Leu Arg Thr Leu Leu Val Gly Val Ile Lys
                165                 170                 175

Pro Glu Ser Pro Ala Thr Ala Ala Ile Leu Ala Ser Lys Asp Pro
                180                 185                 190

Ala Lys Thr Trp Gln Gln Tyr Glu Ala Ser Gly Gly Lys Leu Lys Leu
            195                 200                 205

Asn Val Pro Ala Asn Val Ser Thr Glu Gln Met Lys Val Leu Ser Asp
        210                 215                 220

Asn Glu Lys Leu Met Asp Asp Leu Gly Ala Asn Val Thr Pro Ala Ile
225                 230                 235                 240

Tyr Tyr Met Ser Lys Glu Asn Thr Leu Gln Gln Ala Val Gly Leu Pro
                245                 250                 255

Asp Gln Lys Thr Leu Asn Ile Ile Met Gly Asn Lys
                260                 265

(2) INFORMATION FOR SEQ ID NO:12:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:12:

CGCGCGATAT CATGAAAAAG AATATCGCAT TTCTTCTT                              38

(2) INFORMATION FOR SEQ ID NO:13:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:13:

TCTACGCAAA GCTTTCACGC TGGTCGCATG TTGTCA                                36
```

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutions and modifications apparent to those skilled in the art are deemed to be within the spirit, scope and concept of the invention as defined by the appended claims. Accordingly, the exclusive rights sought to be patented are as described in the claims below.

What is claimed is:

1. A process for producing a heterologous polypeptide in bacteria comprising:

(a) culturing bacterial cells, wherein said bacterial cells comprise an isolated nucleic acid encoding a DsbG protein, nucleic acid encoding the heterologous polypeptide, a signal sequence for secretion of both the DsbG protein and the heterologous polypeptide, and separate inducible promoters for both the nucleic acid encoding the DsbG protein and the nucleic acid encoding the heterologous polypeptide, under conditions whereby expression of the nucleic acid encoding the DsbG protein is induced prior to induction of the expression of the nucleic acid encoding the heterologous polypeptide, and under conditions whereby either both the heterologous polypeptide and the DsbG protein are secreted into the periplasm of the bacteria or the heterologous polypeptide is secreted into the medium in which the bacterial cells are cultured; and (b) recovering the heterologous polypeptide from the periplasm or the culture medium.

2. A method of producing a biologically-active, soluble eukaryotic polypeptide having four or more disulfide bonds, comprising (a) expressing in a bacterial cell an isolated first DNA segment encoding a DsbG protein linked to a signal sequence and a second DNA segment encoding said eukaryotic polypeptide linked to a signal sequence under conditions effective to produce said eukaryotic polypeptide and (b) isolating said soluble eukaryotic polypeptide.

3. A method of producing a biologically-active, heterologous, eukaryotic polypeptide having four or more disulfide bonds, comprising (a) expressing in a bacterial cell an isolated first DNA segment encoding an *E. coli* DsbG protein operatively linked to a signal sequence, and a second DNA segment encoding said heterologous polypeptide operatively linked to a signal sequence, under conditions effective to produce said biologically-active, heterologous, eukaryotic polypeptide and (b) isolating said heterologous eukaryotic polypeptide.

4. A process for producing a correctly folded heterologous eukaryotic polypeptide having four or more disulfide bonds in a bacterial cell, said process comprising (a) expressing in said bacterial cell an isolated first DNA segment encoding an *E. coli* DsbG protein operatively linked to a signal sequence, and a second DNA segment encoding said heterologous polypeptide operatively linked to a signal sequence, under conditions effective to produce said correctly folded heterologous polypeptide and (b) isolating said heterologous eukaryotic polypeptide.

5. A method of producing a biologically-active, recombinant mammalian tissue plasminogen activator polypeptide, comprising (a) expressing in a bacterial cell an isolated first DNA segment encoding a DsbG protein operatively linked to a signal sequence and a second DNA segment encoding a recombinant mammalian tissue plasminogen activator operatively linked to a signal sequence under conditions effective to produce said recombinant mammalian tissue plasminogen activator polypeptide and (b) isolating said tissue plasminogen activator polypeptide.

6. A method of producing a biologically-active, recombinant mammalian pancreatic trypsin inhibitor polypeptide, comprising (a) expressing in a bacterial cell an isolated first DNA segment encoding an *E. coli* DsbG protein operatively linked to a signal sequence and a second DNA segment encoding a recombinant mammalian pancreatic trypsin inhibitor operatively linked to a signal sequence under conditions effective to produce said pancreatic trypsin inhibitor polypeptide and (b) isolating said pacreatic trypsin inhibitor polypeptide.

7. The process of claim 1, wherein the heterologous polypeptide is a mammalian polypeptide.

8. The process of claim 1, wherein the polypeptide is mammalian tissue plasminogen activator.

9. The process of claim 1, wherein the polypeptide is mammalian pancreatic trypsin inhibitor.

10. The process of claim 7, wherein the heterologous polypeptide is insulin-like growth factor.

11. The process of claim 7, wherein the mammalian polypeptide is a human polypeptide.

12. The process of claim 1, wherein the bacterial cells are eubacterial cells.

13. The process of claim 12, wherein the eubacterial cells are Enterobacteriaceae cells.

14. The process of claim 13, wherein the eubacterial cells are *E. coli* cells.

15. The process of claim 1, wherein nucleic acid encoding DsbG is expressed.

16. The process of claim 1, wherein the polypeptide is recovered from the periplasm of the bacterial cells.

17. The process of claim 1, wherein the polypeptide is recovered from the medium.

18. The process of claim 1, wherein after the polypeptide is recovered, the DsbG protein is separated from the polypeptide.

19. The process of claim 1, wherein the culturing is performed in the absence of glutathione.

20. The process of claim 1, wherein yield of total polypeptide is increased as a result of the process, and yield of soluble polypeptide is not changed or is decreased.

21. The process of claim 1, wherein the culturing is carried out without enhanced levels of expression of nucleic acid encoding a heat-shock transcription factor over endogenous levels of expression of said nucleic acid.

22. The process of claim 1, wherein the induction of expression of the nucleic acid encoding DsbG is carried out by adding an inducer to the culture medium.

23. The process of claim 22, wherein the inducer is IPTG, lactose, or L-arabinose.

24. The process of claim 1, wherein the bacterial cells are transformed with one or two expression vectors containing the nucleic acid encoding the DsbG protein and the nucleic acid encoding the heterologous polypeptide.

25. The process of claim 24, wherein the bacterial cells are transformed with two vectors respectively containing the nucleic acid encoding the DsbG protein and the nucleic acid encoding the heterologous polypeptide.

26. The process of claim 24, wherein the nucleic acid encoding DsbG protein and the nucleic acid encoding the heterologous polypeptide are contained on one vector with which the bacterial cells are transformed.

27. The method of claim 2, wherein said DsbG protein is an *E. coli* DsbG protein.

28. The method of claim 2, wherein said signal sequence is an OmpA, Lpp, LamB, MalE, PelB, or StII signal sequence.

29. The method of claim 2, wherein said signal sequence is an OmpA signal sequence.

30. The method of claim 2, wherein said DNA segment is expressed from a lpp-lac, $\lambda_{PL}$, $P_{trc}$, $P_{lac}$, $P_{tac}$, phoA, tet, $P_{BAD}$ or T7 promoter.

31. The method of claim 2, wherein said first and said second DNA segments are expressed from different promoters.

32. The method of claim 2, wherein said DsbG protein is expressed by a vector comprising:

(a) a lac-lpp promoter;

(b) a DNA segment encoding an OmpA signal sequence; and (c) a DNA segment encoding said DsbG protein.

33. The method of claim 2, wherein said recombinant polypeptide comprises six or more disulfide bonds.

34. The method of claim 33, wherein said recombinant polypeptide comprises seventeen or more disulfide bonds.

35. The method of claim 2, wherein said eukaryotic polypeptide is mammalian tissue plasminogen activator.

36. The method of claim 35, wherein said tissue plasminogen activator is human tissue plasminogen activator.

37. The method of claim 35, wherein said tissue plasminogen activator is expressed by a vector comprising a lpp-lac promoter, a DNA segment encoding an OmpA signal sequence, and a DNA segment encoding human tissue plasminogen activator.

38. The method of claim 35, wherein said tissue plasminogen activator is selected from the group consisting of TNK tissue plasminogen activator, PAI-1 tissue plasminogen activator, K2P tissue plasminogen activator, vampire bat tissue plasminogen activator, C84A tissue plasminogen activator, and N-terminally truncated tissue plasminogen activator.

39. The method of claim 2, wherein said eukaryotic polypeptide is secreted from said cell or is isolatable from the periplasm of said cell.

40. The method of claim 2, wherein said recombinant polypeptide is isolatable from a culture supernatant of said bacterial cell.

41. The method of claim 2, wherein said bacterial cell is an Enterobacteriaceae cell.

42. The method of claim 41, wherein said Enterobacteriaceae cell is an Escherichia or Salmonella cell.

43. The method of claim 42, wherein said Escherichia is an SF 103, SF110I, UT5600, or RB791 cell.

44. A bacterial expression system that expresses a DsbG protein, encoded by an isolated DNA, and a eukaryotic recombinant polypeptide having four or more disulfide bonds in a bacterial cell.

45. A bacterial expression system comprising a first expression unit comprising an isolated DNA segment encoding a disulfide isomerase operatively linked to a signal sequence and a second expression unit comprising a DNA segment encoding a recombinant polypeptide having at least about four disulfide bonds operatively linked to a signal sequence, wherein said expression system expresses a DsbG protein and said recombinant polypeptide.

46. A recombinant vector comprising a first transcriptional unit encoding an *E. coli* DsbG protein operatively linked to a signal sequence and said second transcriptional unit comprises a DNA segment encoding a mammalian tissue plasminogen activator or a mammalian pancreatic trypsin inhibitor.

* * * * *

UNITED STATES PATENT AND TRADEMARK OFFICE
CERTIFICATE OF CORRECTION

PATENT NO. : 6,083,715
DATED : July 4, 2000
INVENTOR(S) : Georgiou, Qiu, Bassette, and Swartz It is certified that error appears in the above-identified patent and that said Letters Patent is hereby corrected as shown below:

In item [75], Inventors, please delete "Ji Oiu" and insert -- Ji Qiu -- therefor.

In claim 43, column 51, line 12, please delete "SF110I" and insert -- SF110 -- therefor.

Signed and Sealed this

Twenty-second Day of May, 2001

*Attest:*

NICHOLAS P. GODICI

*Attesting Officer*   Acting Director of the United States Patent and Trademark Office